United States Patent
Satake et al.

(10) Patent No.: US 11,749,390 B2
(45) Date of Patent: *Sep. 5, 2023

(54) DEVICE, SYSTEM, AND METHOD TO QUIT SMOKING

(71) Applicant: CureApp, Inc., Tokyo (JP)

(72) Inventors: Kohta Satake, Tokyo (JP); Shin Suzuki, Tokyo (JP)

(73) Assignee: CureApp, Inc., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/894,434

(22) Filed: Aug. 24, 2022

(65) Prior Publication Data

US 2023/0019848 A1    Jan. 19, 2023

Related U.S. Application Data

(63) Continuation of application No. 17/091,911, filed on Nov. 6, 2020, now Pat. No. 11,462,307, which is a
(Continued)

(51) Int. Cl.
*G16H 10/60* (2018.01)
*G06Q 30/0251* (2023.01)
(Continued)

(52) U.S. Cl.
CPC ......... *G16H 10/60* (2018.01); *G06Q 30/0258* (2013.01); *G06Q 30/0281* (2013.01);
(Continued)

(58) Field of Classification Search
CPC ........ G16H 10/60; G16H 40/63; G16H 20/70; G06Q 50/22; G06Q 30/0283; G06Q 30/0258; G09B 19/00
See application file for complete search history.

(56) References Cited

U.S. PATENT DOCUMENTS 5,813,863 A * 9/1998 Sloane ................... G09B 5/065
434/323
5,879,163 A * 3/1999 Brown .................... G09B 7/04
434/323
(Continued)

*Primary Examiner* — Steve Rowland
(74) *Attorney, Agent, or Firm* — Osha Bergman Watanabe & Burton LLP

(57) ABSTRACT

A non-transitory computer-readable computer medium stores instructions for a patient attempting to quit smoking. The instructions cause a computer to: obtain smoking cessation-related health-care history information of the patient updated by the patient attempting to quit smoking; determine, based on the smoking cessation-related health-care history information, a cognitive-behavioral therapy to be performed, to obtain patient's understanding information about smoking related to the cognitive-behavioral therapy; when a request timing comes, transmit to a patient-side electronic device a patient's understanding information request; receive, from the patient-side electronic device, the patient's understanding information about smoking; determine, by comparing the received patient's understanding information with predetermined correct response information about smoking, whether the patient has a correct patient's understanding about smoking; and when the patient's understanding about smoking is incorrect, transmit, to the patient-side electronic device, cognitive-behavioral therapy information based on the predetermined correct response information.

8 Claims, 19 Drawing Sheets

TREATMENT LIST

| ID | MESSAGE | RESPONSE ALTERNATIVES | CORRECT RESPONSE INFORMATION | | THERAPY TYPE | CONDITION /CAUSE | FOLLOW -UP | SCORE | | | | NUMBER OF DAYS OF THERAPY |
|---|---|---|---|---|---|---|---|---|---|---|---|---|
| | | | CORRECT OPTION | GUIDANCE INFORMATION | | | | CONDITION HISTORY (SMOKING -URGE INDEX) | SMOKING HISTORY | MEDICATION HISTORY | THERAPY HISTORY | |
| 1 | DO YOU THINK THAT STRESS CAN BE RELIEVED BY SMOKING? | 1. ALL OF STRESSES ARE RELIEVED. 2. STRESS CAUSED BY FATIGUE IS RELIEVED. 3. ONLY STRESS CAUSED BY A LACK OF NICOTINE IS RELIEVED. | 3 | STRESS TO BE RELIEVED BY SMOKING IS ONLY STRESS CAUSED BY A LACK OF NICOTINE. STRESS CAUSED BY FATIGUE IS NOT RELIEVED BY SMOKING. | 1 | 1/1 | 5 | - | >1 | - | -1 | - |
| 2 | DO YOU THINK THAT IF YOU DECLINE ACQUAINTANCE'S OFFER, THE ACQUAINTANCE FEELS BAD? | 1. YES 2. NO | 2 | ALMOST NO PERSON FEELS BAD EVEN IF YOU DECLINE HIS/HER OFFER OF CIGARETTES, RATHER, IT IS OFTEN THE CASE THAT HE/SHE SUPPORTS QUITTING SMOKING. | 1 | 1/2 | 5 | - | - | - | -2 | - |
| 3 | DO MILD EXERCISE TO RELIEVE STRESS. | - | - | - | 2 | 1/1 3/0 | 5 | - | - | - | - | - |
| 4 | WHY DON'T YOU GO SHOPPING TO RELIEVE STRESS? | - | - | - | 2 | 1/1 | 5 | - | - | - | - | - |
| 5 | MR/MISS XX DEFINITELY DOES NOT BUCKLE UNDER STRESS! | - | - | - | 3 | 1/1 | - | - | - | - | - | - |
| 6 | WHEN SMOKING URGES ARISE, DO SUBSTITUTIVE BEHAVIOR STRATEGIES! FOR EXAMPLE, CHEW DRIED KELP. | - | - | - | 2 | - | - | 3 | - | - | - | - |

Related U.S. Application Data continuation of application No. 15/569,605, filed as application No. PCT/JP2015/063128 on May 1, 2015, now Pat. No. 10,861,595.

(51) Int. Cl.
*G09B 19/00* (2006.01)
*G09B 7/04* (2006.01)
*G06Q 30/02* (2023.01)
*G16H 40/63* (2018.01)
*G06Q 50/22* (2018.01)
*G16H 20/70* (2018.01)
*G09B 5/06* (2006.01)
*G09B 7/10* (2006.01)

(52) U.S. Cl.
CPC .............. *G06Q 50/22* (2013.01); *G09B 5/065* (2013.01); *G09B 7/04* (2013.01); *G09B 7/10* (2013.01); *G09B 19/00* (2013.01); *G09B 19/0076* (2013.01); *G16H 20/70* (2018.01); *G16H 40/63* (2018.01)

(56) References Cited

U.S. PATENT DOCUMENTS

| | | | | |
|---|---|---|---|---|
| 11,462,307 | B2* | 10/2022 | Satake | G09B 19/00 |
| 2007/0118398 | A1* | 5/2007 | Perls | G16H 10/20 600/300 |
| 2007/0168501 | A1* | 7/2007 | Cobb | G06Q 30/02 709/224 |
| 2008/0230078 | A1* | 9/2008 | Tolman | A24F 47/00 131/270 |
| 2009/0307159 | A1* | 12/2009 | Pinckney | G06N 20/00 706/11 |
| 2011/0172499 | A1* | 7/2011 | Simons-Nikolova | G16H 10/20 600/300 |
| 2014/0087355 | A1* | 3/2014 | Henry | G09B 7/00 434/362 |
| 2014/0156645 | A1* | 6/2014 | Brust | G06F 3/0481 707/722 |
| 2014/0222457 | A1* | 8/2014 | Bosworth | G16H 50/30 705/2 |
| 2016/0029693 | A1* | 2/2016 | Klein | G16H 20/70 434/236 |
| 2016/0148530 | A1* | 5/2016 | Dayan | G09B 7/00 434/236 |
| 2016/0278435 | A1* | 9/2016 | Choukroun | A24F 40/50 |
| 2016/0371464 | A1* | 12/2016 | Bricker | G16H 20/30 |
| 2018/0075219 | A1* | 3/2018 | Klein | G16H 20/70 |

\* cited by examiner

FIG.10

| PATIENT INFORMATION | | | | SMOKING CESSATION-RELATED HEALTH-CARE HISTORY INFORMATION | | | | |
|---|---|---|---|---|---|---|---|---|
| ID | PERSONAL INFORMATION | | DURATION OF SMOKING (YEAR) | NUMBER OF DAYS OF THERAPY | CONDITION HISTORY (SMOKING-URGE INDEX) | SMOKING HISTORY | MEDICATION HISTORY | THERAPY HISTORY |
| | NAME | AGE | | | | | | |
| 1 | AAAA | 30 | 5 | 24 | 2015/3/1 15 2015/3/1 25 2015/3/1 3:4 ⋮ 2015/4/1 0 2015/4/2 0 2015/4/3 0:0 | 2015/3/1 10 2015/3/1 23 2015/3/1 3:2 ⋮ 2015/4/1 0 2015/4/2 0 2015/4/3 0:0 | 2015/3/1 11 2015/3/1 20 2015/3/1 3:1 ⋮ 2015/4/1 1 2015/4/2 1 2015/4/3 0:1 | 2015/3/1 19 2015/3/1 2 18 2015/3/1 3:20 ⋮ 2015/4/1 14 2015/4/2 3 2015/4/3 0:4 |
| 2 | BBBB | 42 | 20 | 8 | ⋮ 2015/4/1 15 2015/4/2 25 2015/4/3 0:4 | ⋮ 2015/4/1 2 2015/4/2 2 2015/4/3 0:1 | ⋮ 2015/4/1 1 2015/4/2 1 2015/4/3 0:1 | ⋮ 2015/4/1 1 2015/4/2 2 2015/4/3 10 |
| ⋮ | ⋮ | ⋮ | ⋮ | | ⋮ | ⋮ | ⋮ | ⋮ |

FIG.11A

TREATMENT LIST

| ID | MESSAGE | RESPONSE ALTERNATIVES | CORRECT RESPONSE INFORMATION | | THERAPY TYPE | CONDITION /CAUSE | FOLLOW -UP | SCORE | | | | |
|---|---|---|---|---|---|---|---|---|---|---|---|---|
| | | | CORRECT OPTION | GUIDANCE INFORMATION | | | | CONDITION HISTORY (SMOKING -URGE INDEX) | SMOKING HISTORY | MEDICATION HISTORY | THERAPY HISTORY | NUMBER OF DAYS OF THERAPY |
| 1 | DO YOU THINK THAT STRESS CAN BE RELIEVED BY SMOKING? | 1. ALL OF STRESSES ARE RELIEVED. 2. STRESS CAUSED BY FATIGUE IS RELIEVED. 3. ONLY STRESS CAUSED BY A LACK OF NICOTINE IS RELIEVED. | 3 | STRESS TO BE RELIEVED BY SMOKING IS ONLY STRESS CAUSED BY A LACK OF NICOTINE. STRESS CAUSED BY FATIGUE IS NOT RELIEVED BY SMOKING. | 1 | 1/1 | 5 | - | >1 | - | -1 | - |
| 2 | DO YOU THINK THAT IF YOU DECLINE ACQUAINTANCE'S OFFER, THE ACQUAINTANCE FEELS BAD? | 1. YES 2. NO | 2 | ALMOST NO PERSON FEELS BAD EVEN IF YOU DECLINE HIS/HER OFFER OF CIGARETTES. RATHER, IT IS OFTEN THE CASE THAT HE/SHE SUPPORTS QUITTING SMOKING. | 1 | 1/2 | 5 | - | - | - | -2 | - |
| 3 | DO MILD EXERCISE TO RELIEVE STRESS. | - | - | - | 2 | 1/1 3/0 | 5 | - | - | - | - | - |
| 4 | WHY DON'T YOU GO SHOPPING TO RELIEVE STRESS? | - | - | - | 2 | 1/1 | 5 | - | - | - | - | - |
| 5 | MR/MISS XX DEFINITELY DOES NOT BUCKLE UNDER STRESS! | - | - | - | 3 | 1/1 | - | - | - | - | - | - |
| 6 | WHEN SMOKING URGES ARISE, DO SUBSTITUTIVE BEHAVIOR STRATEGIES! FOR EXAMPLE, CHEW DRIED KELP. | - | - | - | 2 | - | - | 3 | - | - | - | - |

FIG.11B

TREATMENT LIST

| ID | MESSAGE | RESPONSE ALTERNATIVES | CORRECT RESPONSE INFORMATION | | THERAPY TYPE | CONDITION /CAUSE | FOLLOW-UP | SCORE | | | | |
|---|---|---|---|---|---|---|---|---|---|---|---|---|
| | | | CORRECT OPTION | GUIDANCE INFORMATION | | | | CONDITION HISTORY (SMOKING-URGE INDEX) | SMOKING HISTORY | MEDICATION HISTORY | THERAPY HISTORY | NUMBER OF DAYS OF THERAPY |
| 7 | DO YOU THINK THAT THERE IS NO HARM IN SMOKING ONE CIGARETTE? | 1. YES<br>2. NO | 2 | PLEASE RECOGNIZE THAT "SMOKING JUST ONE CIGARETTE" DOES NOT SIMPLY MEAN "SMOKING ONLY ONCE" BUT RESULTS IN A SITUATION WHERE YOUR BRAIN RETURNS TO A NICOTINE-DEPENDENT STATE. | 1 | - | - | 0*3 | 0*3 | 1*3 | 12 | 28>><br>21 |
| 8 | YOU SHOULD PREPARE A SPECIFIC WAY TO DECLINE OFFER OF CIGARETTES. | - | - | - | 2 | - | 5 | - | - | - | 2 | - |
| 9 | DO YOU THINK THAT IT IS A GOOD WAY TO TENTATIVELY RELIEVE HEADACHE BY SMOKING A CIGARETTE? | 1. YES<br>2. NO | 2 | THE OCCURRENCE OF HEADACHE DUE TO A LACK OF NICOTINE IS A SYMPTOM OCCURRING IN A COURSE IN WHICH YOUR BRAIN CHANGES TO A NORMAL STATE, AND IS A TEMPORARY SYMPTOM. IF YOU SMOKE A CIGARETTE NOW, YOUR BRAIN WILL RETURN TO A NICOTINE-DEPENDENT STATE. | 1 | 2/1 | 5 | - | - | - | - | - |
| ⋮ | ⋮ | ⋮ | ⋮ | ⋮ | ⋮ | ⋮ | ⋮ | ⋮ | ⋮ | ⋮ | ⋮ | ⋮ |

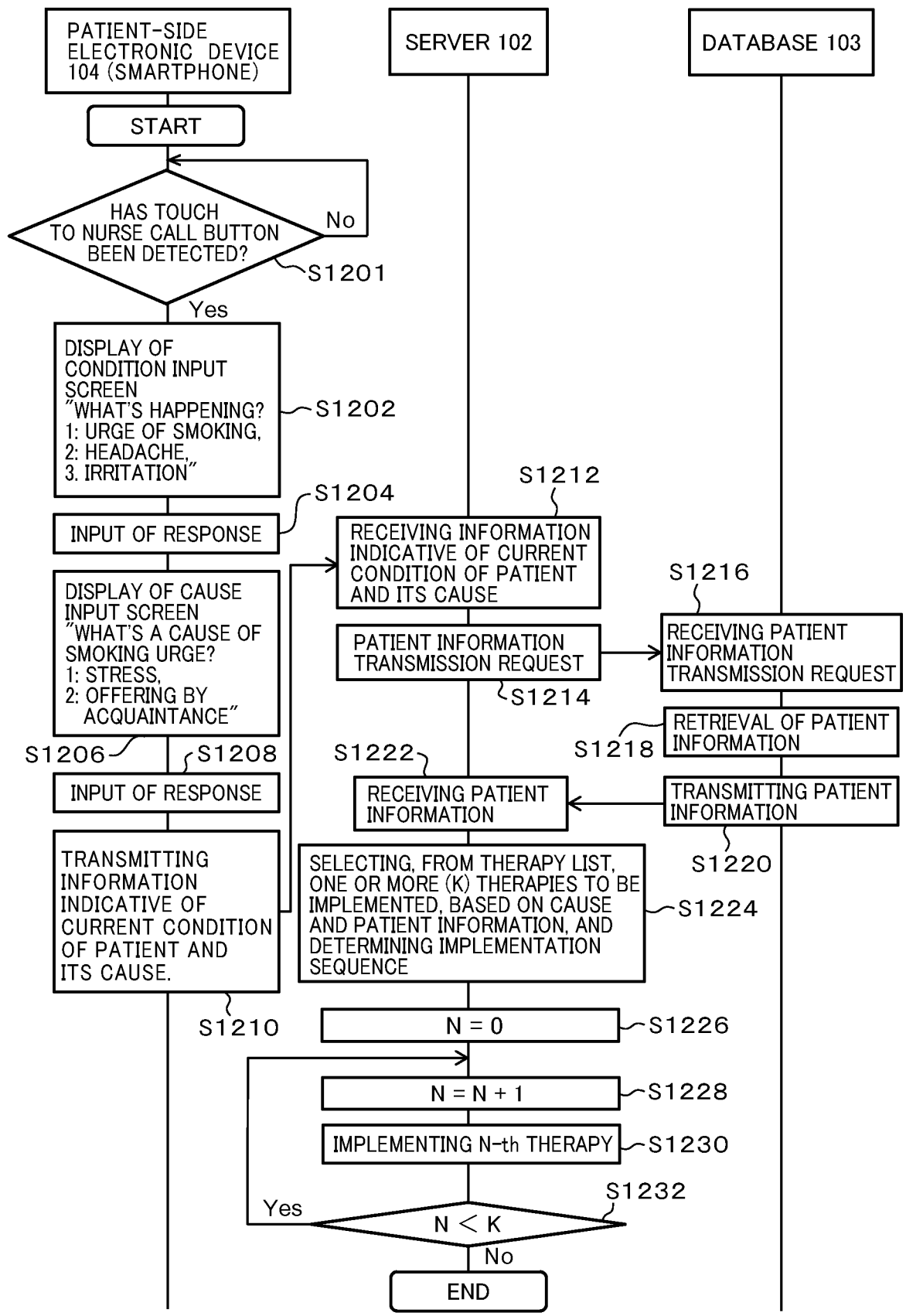

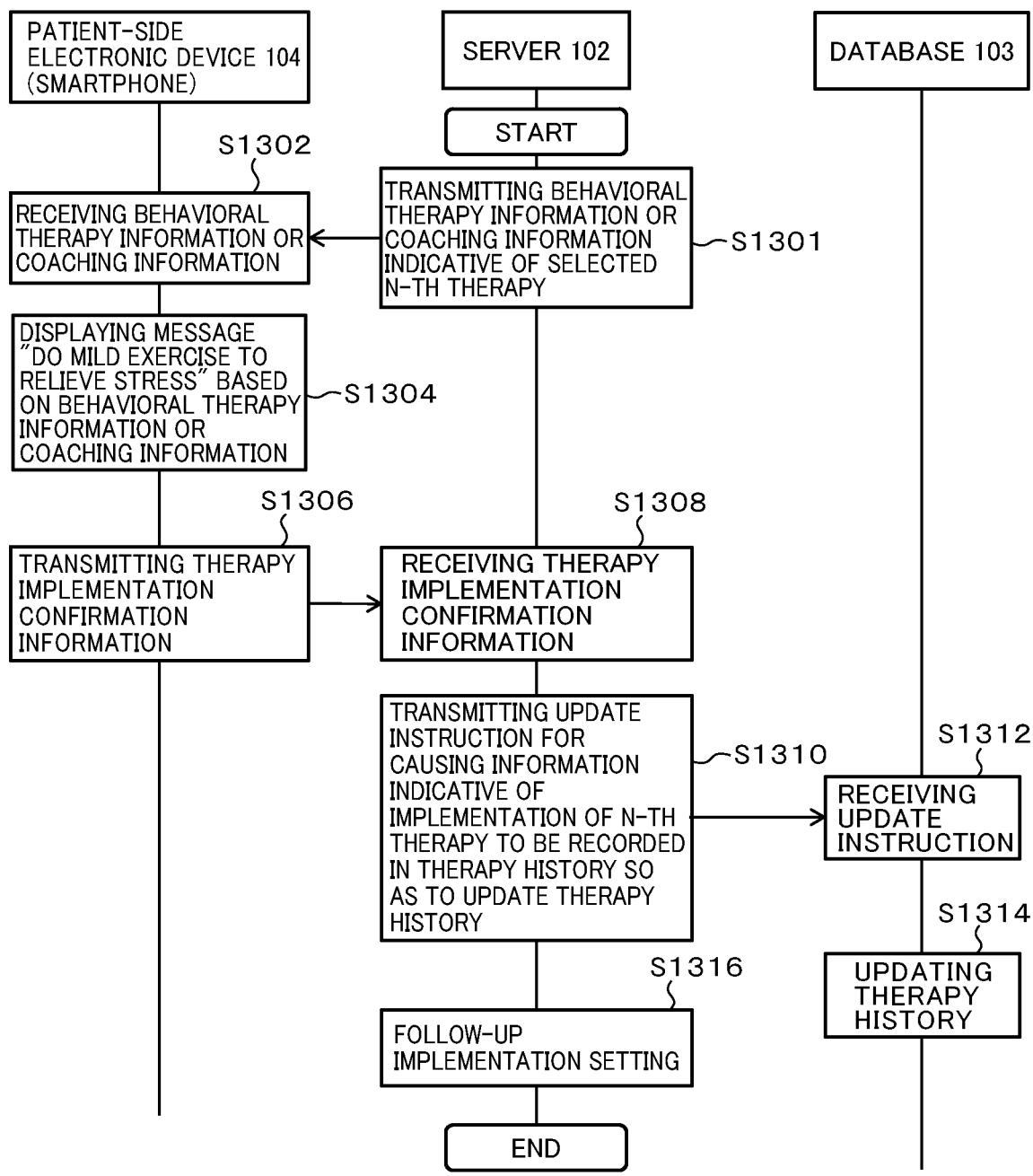

DEVICE, SYSTEM, AND METHOD TO QUIT SMOKING

TECHNICAL FIELD

The present invention relates to a device, a system and a method for a patient who is attempting to quit smoking.

BACKGROUND ART

It is not always easy for a person who has continued to smoke to kick the smoking habit. A nicotine-dependent state caused by continuous smoking is classified into two states: physical dependence; and psychological dependence. Generally, for the physical nicotine dependence, a drug or pharmacological therapy using a smoking-cessation aid such as varenicline or nicotine preparation is performed, and, for the psychological nicotine dependence, a behavioral therapy, cognitive-behavioral therapy and coaching by a health professional are performed. The behavioral therapy means a therapeutic procedure in which a health professional prompts a patient to practice a behavior (therapeutic behavior) which is expected to produce a therapeutic effect when implemented. Among various types of behavioral therapies, a therapeutic procedure in which, when a smoking urge, i.e., an urge to smoke, occurs, a certain action other than a smoking action is performed to thereby avoid a smoking action, is referred to as "substitute behavioral therapy". The cognitive-behavioral therapy means a therapeutic procedure in which a gap between patient's understanding (cognition) and a fact from a scientific standpoint (a gap in cognition) is corrected to thereby make a patient's behavioral change. The coaching means providing to a patient knowledge pertaining to diseases to thereby educate, encourage or praise the patient.

In the following Prior Art Document 1, there is proposed a system for transmitting every day a message for supporting an individual person who wishes to improve health-related behavior such as smoking cessation, body weight control or stress management.

CITATION LIST

Patent Document

Patent Document 1: JP 2001-092876 A

As to a result of therapy using varenicline, although a 3-month smoking cessation success rate is about 65%, many persons will restart smoking, and consequently a one-year smoking cessation success rate is only about 35%. Persons who successfully stop smoking once by a pharmacological therapy will restart smoking at a high rate. This is probably because psychological dependence has not been resolved. Psychological dependence is a mental disorder, and requires daily detailed supports by a health professional or the like. However, a health professional can be involved only at each outpatient visit. There are often the cases where the total number, frequency, period, etc., of outpatient services which can be taken within health-care services covered by health insurance are limited. For example, in Japan, the number of outpatient services which can be taken within health-care services covered by health insurance is only five, and the frequency of the outpatient services is about one time two weeks to one month. Thus, the entire therapy will be terminated within about three months. Moreover, outpatient service hours are also limited, so that it is often the case that, even when a patient who is attempting to quit smoking decides to consult a medical doctor, it is necessary to take long time until he/she sees a medical doctor, because he/she has to go to a hospital. After the outpatient service hours, it is impossible to consult a medical doctor in the first place. As above, a time usable for smoking cessation coaching by a health professional is extremely limited, and a patient with nicotine dependence cannot consult a health professional when he/she wishes to do so, and it is difficult to receive smoking cessation therapy over a long period of time. Further, quality in smoking cessation coaching varies depending on medical institutions or health professionals.

The system disclosed in the Prior Art Document 1 is configured to provide on a day-to-day basis a behavior modification message for improving health-related bad behavior, based on data collected from an individual person. The use of this system enables a patient to receive the behavior modification message once a day, so that the patient can understand a behavior to be taken on the day. However, it is impossible to finely tune a therapy to be implemented, depending on patient's smoking cessation therapeutic situation which varies from hour to hour. Moreover, for a patient who is attempting to quit smoking and is psychologically dependent on smoking, like psychological nicotine dependence, the behavior modification message to be transmitted once a day is not enough, i.e., fails to timely implement a therapy suitable for a patient's psychological state on a moment-to-moment basis. Further, it is impossible to solve the problem that a patient cannot consult a medical doctor when he/she wishes to do so.

Technical Advantages

One or more embodiments of the present invention can provide one or more of the following technical advantages that, when executed by a computer or computer system, improve the functionality of the computer system over conventional technology. According to a first aspect of the present invention, there is provided a program executable by a computer designed to be used for a patient who is attempting to quit smoking. The program is configured to cause the computer to execute the steps of: receiving, from a patient-side electronic device which is an electronic device used by the patient, patient's understanding information input into the patient-side electronic device by the patient and indicative of understanding of the patient about a given smoking-related matter, at a patient's understanding information acquisition timing decided based on at least one of an input of information indicative of a current condition of the patient, and smoking cessation-related health-care history information of the patient; deciding, based on the received patient's understanding information and correct response information about the smoking-related matter, whether or not the patient's understanding about the smoking-related matter is incorrect; and, when the patient's understanding is decided to be incorrect, transmitting cognitive-behavioral therapy information based on the correct response information to the patient-side electronic device, wherein the cognitive-behavioral therapy information includes information for the patient which is deemed to be correct with respect to the smoking-related matter.

The program according to the first aspect of the present invention is configured to cause the computer to further execute the steps of: reading the smoking cessation-related health-care history information from a database; based on the received smoking cessation-related health-care history information, deciding a request timing of requesting the patient-side electronic device to transmit the patient's understanding information including the patient's understanding about the given smoking-related matter; and at the request timing, transmitting, to the patient-side electronic device, a patient's understanding information request for requesting transmission of the patient's understanding information including the patient's understanding about the given smoking-related matter, wherein the patient's understanding information acquisition timing is a timing of receiving the patient's understanding information as a response to the patient's understanding information request.

In the program according to the first aspect of the present invention, the patient's understanding information acquisition timing is decided based on a timing at which information indicative of a current condition of the patient is input into the patient-side electronic device, wherein the program is configured to cause the computer to further execute the step of, at a condition information acquisition timing decided based on the timing at which information indicative of a current condition of the patient is input into the patient-side electronic device, acquiring the information indicative of a current condition of the patient, and wherein the patient's understanding information includes information indicative of an association between the current condition of the patient and smoking, estimated by the patient.

The above program is configured to cause the computer to further execute the step of, at a first behavioral therapy implementation timing decided based on the timing at which the information indicative of the current condition of the patient is input into the patient-side electronic device, transmitting first behavioral therapy information based on the information indicative of the current condition of the patient, wherein the first behavioral therapy information is indicative of a behavior to be taken by the patient in connection with the current condition of the patient.

The information indicative of the current condition of the patient may include a cause of the current condition of the patient estimated by the patient.

The above program is configured to cause the computer to further execute the steps of: after transmitting the first behavioral therapy information, transmitting effect-related inquiry information indicative of a message for inquiring about whether or not the condition is improved; in response to the effect-related inquiry information, receiving effect-related response information indicative of a response input by the patient; and when the effect-related response information indicates that the condition is not improved, transmitting second behavioral therapy information indicative of a behavior to be taken by the patient in connection with the condition.

The step of transmitting cognitive-behavioral therapy information may be executed after execution of the step of transmitting the first behavioral therapy information.

The above program is configured to cause the computer to further execute the step of, at a coaching timing decided based on the timing at which the information indicative of the current condition of the patient is input into the patient-side electronic device, transmitting coaching information indicative of a massage for encouraging the patient in connection with the condition of the patient.

The step of transmitting cognitive-behavioral therapy information may be executed after execution of the step of transmitting the coaching information.

The program according to the first aspect of the present invention is configured to cause the computer to further execute the steps of: based on at least one of an input of information indicative of a current condition of the patient, and the smoking cessation-related health-care history information of the patient, deciding a second behavioral therapy implementation timing, and deciding third behavioral therapy information indicative of a behavior to be taken by the patient for the purpose of smoking cessation therapy; at the second behavioral therapy implementation timing, transmitting the third behavioral therapy information to the patient-side electronic device; and updating the smoking cessation-related health-care history information, based on at least one of the cognitive-behavioral therapy information and the third behavioral therapy information.

The program according to the first aspect of the present invention is configured to cause the computer to further execute the steps of: after transmitting the cognitive-behavioral therapy information, updating the smoking cessation-related health-care history information, based on the patient's understanding information and the cognitive-behavioral therapy information; and based on the updated smoking cessation-related health-care history information, transmitting information about medication adjustment, to at least one of a doctor-side electronic device used by a medical doctor and the patient-side electronic device.

According to a second aspect of the present invention, there is provided a computer-readable recording medium storing therein the program according to the first aspect of the present invention.

According to a third aspect of the present invention, there is provided a computer comprising a processing unit, a communication unit, and a storage unit storing therein a program designed to be used for a patient who is attempting to quit smoking, wherein the program is configured to cause the computer to execute the steps of: receiving, from a patient-side electronic device which is an electronic device used by the patient, patient's understanding information input into the patient-side electronic device by the patient and indicative of understanding of the patient about a smoking-related matter, at a patient's understanding information acquisition timing decided based on at least one of an input of information indicative of a current condition of the patient, and smoking cessation-related health-care history information of the patient; deciding, based on the received patient's understanding information and correct response information about the smoking-related matter, whether or not the patient's understanding about the smoking-related matter is incorrect; and when the patient's understanding is decided to be incorrect, transmitting cognitive-behavioral therapy information based on the correct response information to the patient-side electronic device, wherein the cognitive-behavioral therapy information includes information for the patient which is deemed to be correct with respect to the smoking-related matter.

According to a fourth aspect of the present invention, there is provided a computer designed to be used for a patient who is attempting to quit smoking. The computer comprises: a communication section operable to receive, from a patient-side electronic device which is an electronic device used by the patient, patient's understanding information input into the patient-side electronic device by the patient and indicative of understanding of the patient about a smoking-related matter, at a patient's understanding information acquisition timing decided based on at least one of an input of information indicative of a current condition of the patient, and smoking cessation-related health-care history information of the patient, and, when the patient's understanding is decided to be incorrect, to transmit cognitive-behavioral therapy information based on correct response information about the smoking-related matter to the patient-side electronic device, the cognitive-behavioral therapy information including information for the patient which is deemed to be correct with respect to the smoking-related matter; and a control section operable to decide, based on the received patient's understanding information and the correct response information, whether or not the patient's understanding about the smoking-related matter is incorrect.

According to a fifth aspect of the present invention, there is provided a program executable by an electronic device designed to be used for a patient who is attempting to quit smoking. The program is configured to cause the electronic device used by the patient to execute the steps of: accepting an input of patient's understanding information indicative of understanding of the patient about a smoking-related matter, at a patient's understanding information acquisition timing decided based on at least one of an input of information indicative of a current condition of the patient, and smoking cessation-related health-care history information of the patient; transmitting the input patient's understanding information to a server; when the patient's understanding is decided to be incorrect, receiving, from the server, cognitive-behavioral therapy information including information for the patient indicative of information deemed to be correct with respect to the smoking-related matter; and based on the received cognitive-behavioral therapy information, presenting the information deemed to be correct with respect to the smoking-related matter, to the patient.

According to a sixth aspect of the present invention, there is provided a patient-side electronic device designed to be used for a patient who is attempting to quit smoking. The electronic device comprises a processing unit, a communication unit, an output unit, and a storage unit storing therein a program designed to be used for a patient who is attempting to quit smoking, wherein the program is configured to cause the electronic device to execute the steps of: accepting an input of patient's understanding information indicative of understanding of the patient about a smoking-related matter, at a patient's understanding information acquisition timing decided based on at least one of an input of information indicative of a current condition of the patient, and smoking cessation-related health-care history information of the patient; transmitting the input patient's understanding information to a server; when the patient's understanding is decided to be incorrect, receiving, from the server, cognitive-behavioral therapy information including information for the patient indicative of information deemed to be correct with respect to the smoking-related matter; and based on the received cognitive-behavioral therapy information, presenting the information deemed to be correct with respect to the smoking-related matter, to the patient.

According to a seventh aspect of the present invention, there is provided a patient-side electronic device designed to be used for a patient who is attempting to quit smoking. The electronic device comprises: an input section operable to accept an input of patient's understanding information indicative of understanding of the patient about a smoking-related matter, at a patient's understanding information acquisition timing decided based on at least one of an input of information indicative of a current condition of the patient, and smoking cessation-related health-care history information of the patient; a communication section operable to transmit the input patient's understanding information to a server, and, when the patient's understanding is decided to be incorrect, to receive, from the server, cognitive-behavioral therapy information including information for the patient indicative of information deemed to be correct with respect to the smoking-related matter; and an output section operable, based on the received cognitive-behavioral therapy information, to present the information deemed to be correct with respect to the smoking-related matter, to the patient.

According to an eighth aspect of the present invention, there is provided a system designed to be used for a patient who is attempting to quit smoking. The system comprises: a server composed of the computer according to the third or fourth aspect of the present invention; at least one electronic device used by the patient, composed of the electronic device according to the sixth or seventh aspect of the present invention; and a database storing therein the smoking cessation-related health-care history information of the patient.

According to a ninth aspect of the present invention, there is provided a method designed to be used for a patient who is attempting to quit smoking. The method comprises causing a computer to execute the steps of: receiving, from a patient-side electronic device which is an electronic device used by the patient, patient's understanding information input into the patient-side electronic device by the patient and indicative of understanding of the patient about a given smoking-related matter, at a patient's understanding information acquisition timing decided based on at least one of an input of information indicative of a current condition of the patient, and smoking cessation-related health-care history information of the patient; deciding, based on the received patient's understanding information and correct response information about the smoking-related matter, whether or not the patient's understanding about the smoking-related matter is incorrect; and when the patient's understanding is decided to be incorrect, transmitting cognitive-behavioral therapy information based on the correct response information to the patient-side electronic device, wherein the cognitive-behavioral therapy information includes information for the patient which is deemed to be correct with respect to the smoking-related matter.

According to a tenth aspect of the present invention, there is provided a method designed to be used for a patient who is attempting to quit smoking. The method comprises causing an electronic device to execute the steps of: accepting an input of patient's understanding information indicative of understanding of the patient about a smoking-related matter, at a patient's understanding information acquisition timing decided based on at least one of an input of information indicative of a current condition of the patient, and smoking cessation-related health-care history information of the patient; transmitting the input patient's understanding information to a server; when the patient's understanding is decided to be incorrect, receiving, from the server, cognitive-behavioral therapy information including information for the patient indicative of information deemed to be correct with respect to the smoking-related matter; and based on the received cognitive-behavioral therapy information, presenting the information deemed to be correct with respect to the smoking-related matter, to the patient.

One or more embodiments of the present invention provide an improvement over existing computer-implemented technologies by making it possible to select an appropriate therapy and delicately change a timing of implementing the selected therapy, depending on patient's smoking cessation therapeutic situation which varies from hour to hour, and timely implement a necessary therapy when needed. The patient can use an electronic device such as his/her own smartphone to receive smoking cessation therapy daily and for a long period of time via the electronic device. Thus, it is possible to effectively provide therapy for a patient who is attempting to quit smoking, in particular, who psychological depends on smoking. In addition, by setting a system so as to enable the system to select and implement an appropriate therapy, it becomes possible to constantly realize an appropriate smoking cessation coaching without any variation.

The patient can input information indicative of a current condition of the patient, such as smoking urge or withdrawal symptom, via his/her own electronic device. In the case where this information is used to select and implement a therapy, the patient's understanding about the smoking-related matter, i.e., an association between the condition and its cause, is specified, and, when the patient's understanding is incorrect, the understanding is straightened out to thereby improve the current condition, and enable the patient to have correct knowledge about smoking. This makes it possible to correct an incorrect thinking pattern of the patient to enable the patient to think based on correct understanding when the patient has the same condition. For example, it is possible to effectively prevent the occurrence of a situation where smoking urges occur based on incorrect understanding, resulting in smoking. Further, when a cause of the current condition can be additionally specified, it becomes possible to implement therapy appropriate to the cause. When the current condition is smoking urge, behavioral therapy appropriate to the specified cause of the smoking urges, such as substitutive behavioral therapy, can be performed in combination with coaching to more effectively relieve smoking urges. This makes it possible to effectively prevent the occurring of a situation where a patient who is attempting to quit smoking smokes due to temporary strong smoking urge and returns to a state before start of the smoking cessation therapy.

BRIEF DESCRIPTION OF DRAWINGS

FIG. 10 is a patient information table in the system according to this embodiment.

FIG. 11A is a therapy list in the system according to this embodiment.

FIG. 11B is a therapy list in the system according to this embodiment.

FIG. 12 is a flowchart depicting a process in a system according a first embodiment of the present invention.

FIG. 13 is a flowchart depicting the process in the system according the first embodiment of the present invention.

DESCRIPTION OF EMBODIMENTS

Figure 1:
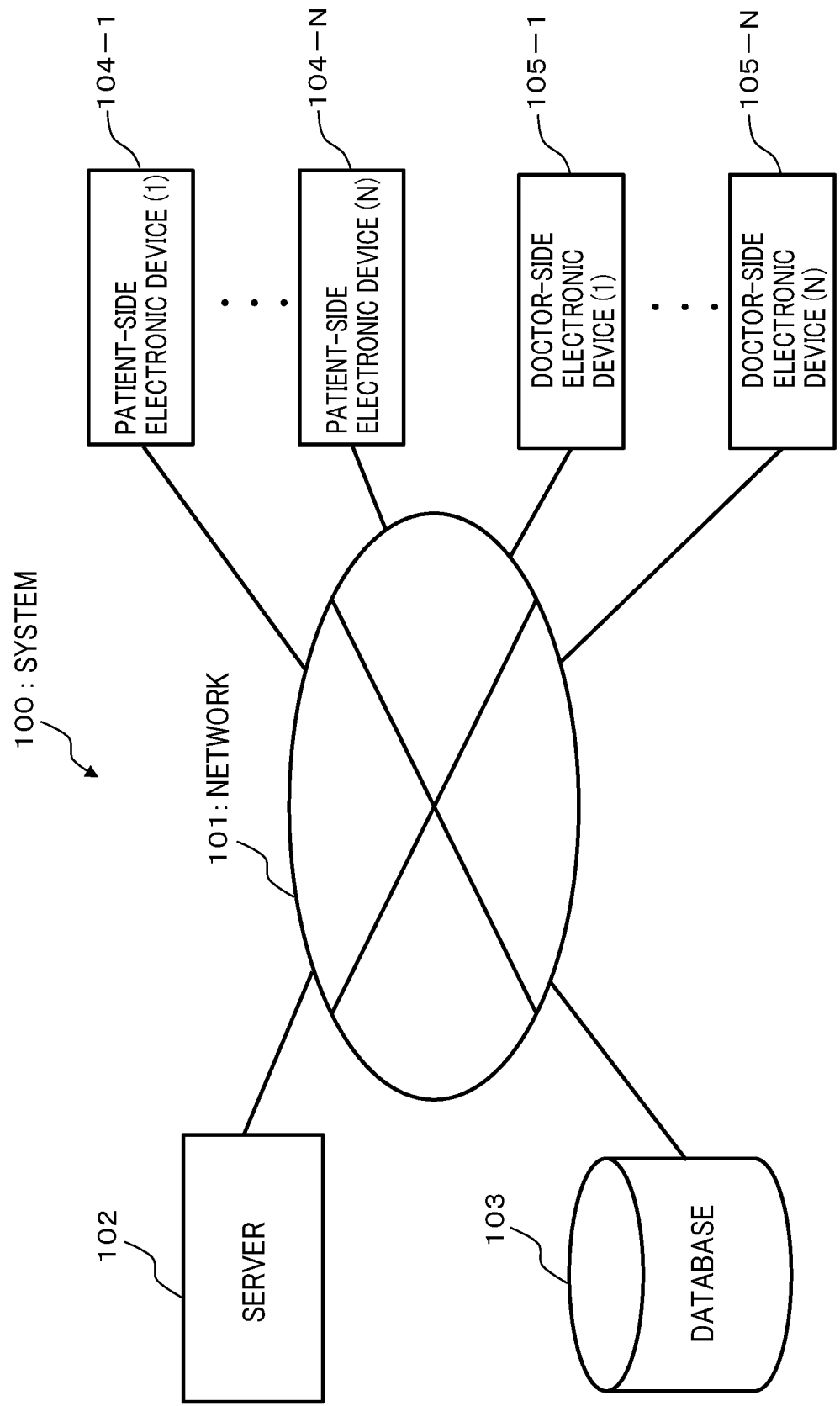
FIG. 1 is a block diagram depicting a configuration of a system according to one embodiment of the present invention.

FIG. 1 depicts a configuration of a system according to one embodiment of the present invention. This system 100 is designed to be used for a patient who is attempting to quit smoking, and comprises: a server 102; a database 103; one or more patient-side electronic devices 104 (104-1 to 104-N) each of which is an electronic device used by the patient; and one or more doctor-side electronic devices 105 (105-1 to 105-N) each of which is an electronic device used by a doctor. In this embodiment, these components are connected to each other via a network 101. Alternatively, the system may be configured such that they are connected to each other individually as needed basis. For example, the system may be configured such that the database 103 is directly connected to the server 102 without being connected to the network 101, and the patient-side electronic devices 104-1 to 104-N and the doctor-side electronic devices 105-1 to 105-N are connected to the database 103 via the server 102.

Figure 2:
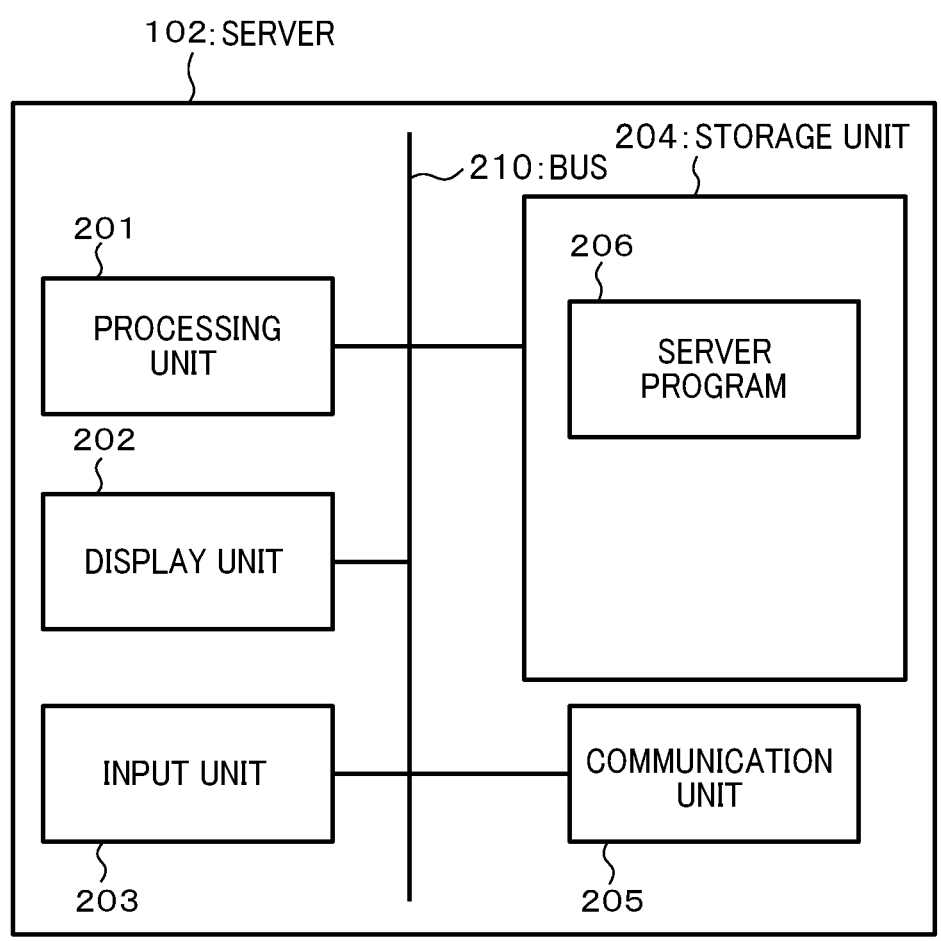
FIG. 2 is a block diagram depicting a hardware configuration of a server in the system according to this embodiment.

FIG. 2 depicts a hardware configuration of the server 102 in the system according to this embodiment. The server 102 is a computer comprising a processing unit 201, a display unit 202, an input unit 203, a storage unit 204, and a communication unit 205. In this embodiment, these units are connected to each other via a bus 210. Alternatively, the server may be configured such that they are connected to each other individually as needed basis. The display unit 202 has a function of displaying information to a user. The input unit 203 has a function of accepting an input from a user, like a keyboard, a mouse or the like. The storage unit 204 stores therein a server program 206. The storage unit 204 may be any type of storage unit, such as a non-volatile memory or a volatile memory, as long as it is capable of storing information therein. The communication unit 205 is operable to perform wire communication using an Ethernet (trademark) cable or the like, or wireless communication using cellular network, wireless LAN or the like, to establish connection to the network 101.

Figure 3:
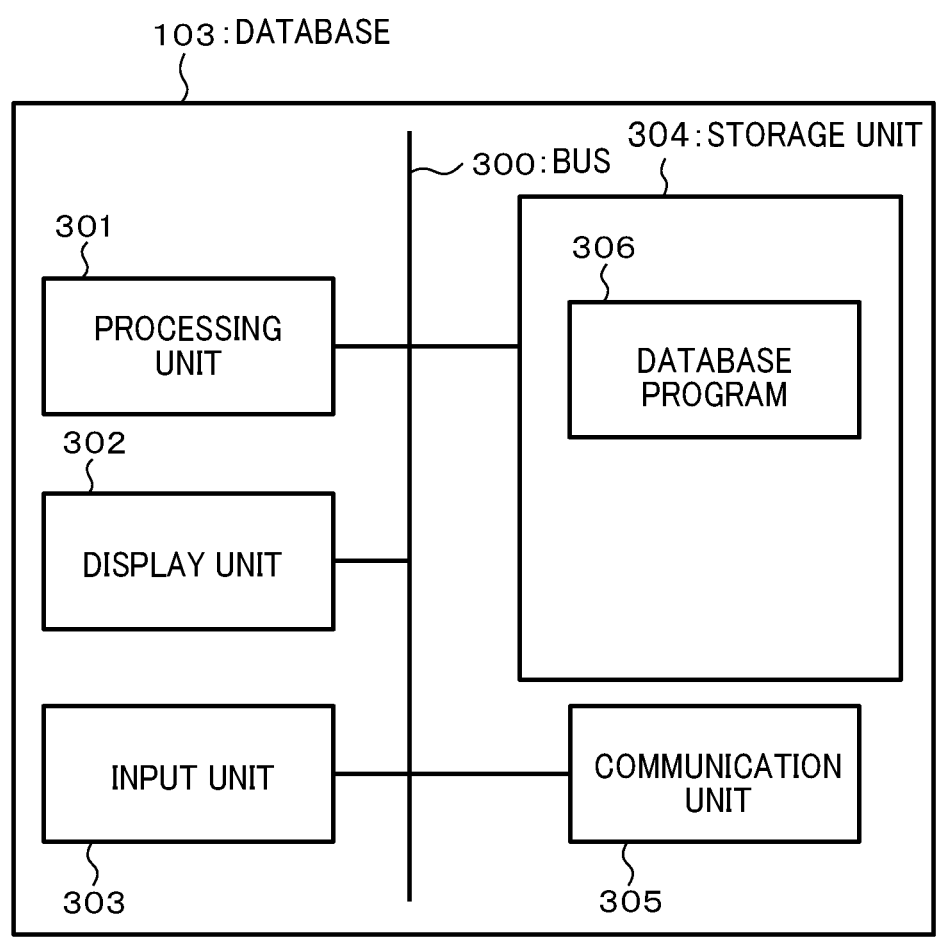
FIG. 3 is a block diagram depicting a hardware configuration of a database in the system according to this embodiment.

FIG. 3 depicts a hardware configuration of the database 103 in the system according to this embodiment. The database 103 is a computer comprising a processing unit 301, a display unit 302, an input unit 303, a storage unit 304, and a communication unit 305. In this embodiment, these units are connected to each other via a bus 310. Alternatively, the database 103 may be configured such that they are connected to each other individually as needed basis. The display unit 302 has a function of displaying information to a user. The input unit 303 has a function of accepting an input from a user, like a keyboard, a mouse or the like. The storage unit 304 may be any type of storage unit, such as a non-volatile memory or a volatile memory, as long as it is capable of storing information therein. The storage unit 304 stores therein a database (DB) program 306. The communication unit 305 is operable to perform wire communication using an Ethernet (trademark) cable or the like, or wireless communication using cellular network, wireless LAN or the like, to establish connection to the network 101.

In this embodiment, the server 102 and the database 103 are realized by different computers. Alternatively, they may be realized by a single computer.

Figure 4:
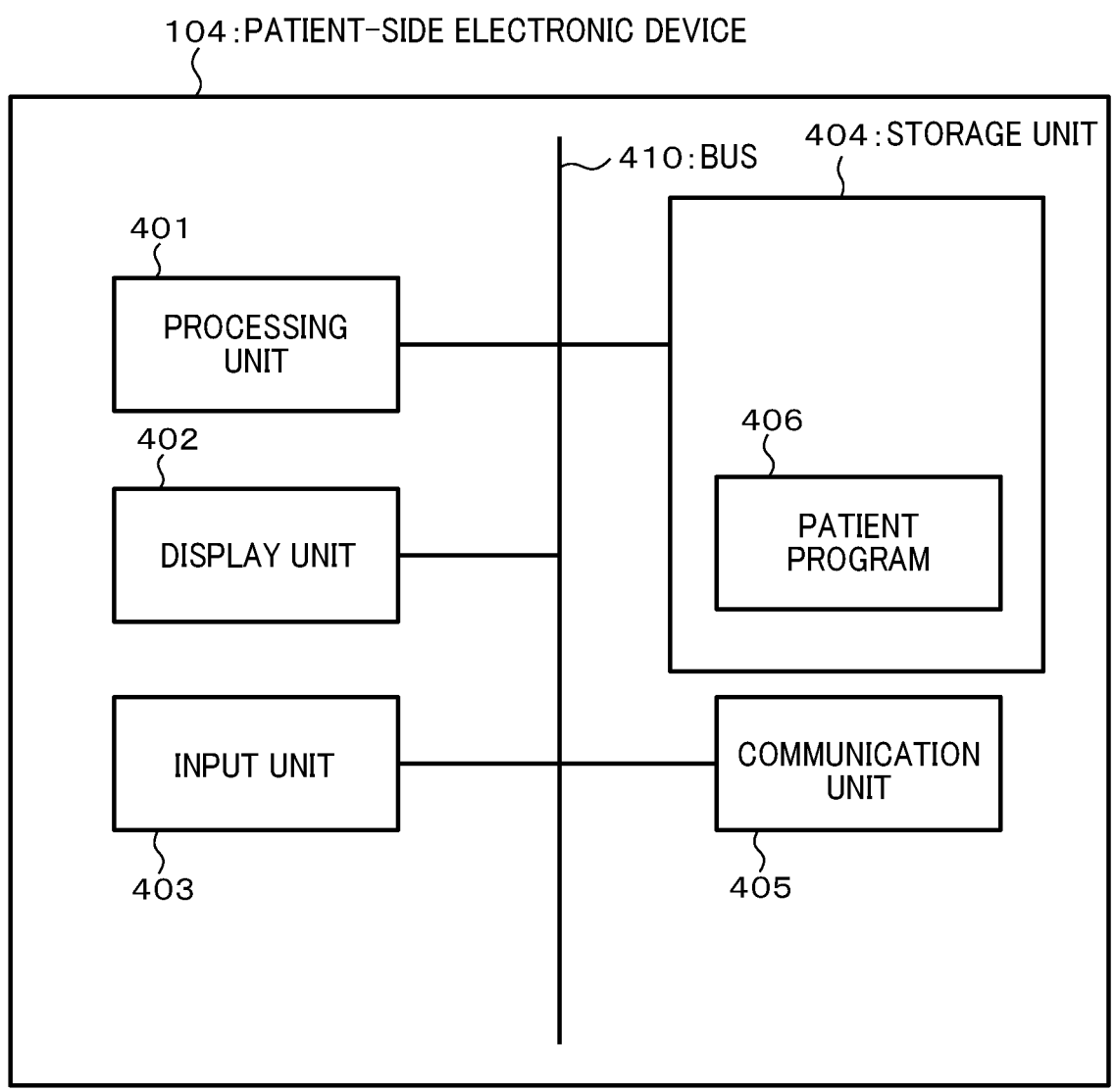
FIG. 4 is a block diagram depicting a hardware configuration of a patient-side electronic device in the system according to this embodiment.

FIG. 4 is a block diagram depicting a hardware configuration of the patient-side electronic device 104 which is an electronic device used by a patient, in the system according to this embodiment. As used herein, the term "patient" means a person who is attempting to quit smoking, but does not necessarily mean a person who is undergoing smoking cessation therapy supervised by a health professional. The patient-side electronic device 104 comprises a processing unit 401, a display unit 402, an input unit 403, a storage unit 404, and a communication unit 405. In this embodiment, these units are connected to each other via a bus 410. Alternatively, the patient-side electronic device may be configured such that they are connected to each other individually as needed basis. The patient-side electronic device 104 may be composed of a desktop computer or a notebook computer, or may be a personal digital assistance, a mobile phone, a smartphone or a tablet terminal, or may be a dedicated portable electronic device. From a viewpoint of enabling a patient to promptly input his/her condition, it may be composed of a portable communication terminal. The display unit 402 has a function of displaying information to a user. The input unit 403 has a function of accepting an input from a user, like a keyboard, a mouse or the like. When the patient-side electronic device 104 is composed of a smart phone or a tablet terminal, the display unit 402 and the input unit 403 may be integrated together as a touch panel. The storage unit 404 stores therein a patient program 406 for the patient-side electronic device. The storage unit 404 may be any type of storage unit, such as a non-volatile memory or a volatile memory, as long as it is capable of storing information therein. The communication unit 405 is operable to perform wire communication using an Ethernet (trademark) cable or the like, or wireless communication using cellular network, wireless LAN or the like, to establish connection to the network 101.

Figure 5:
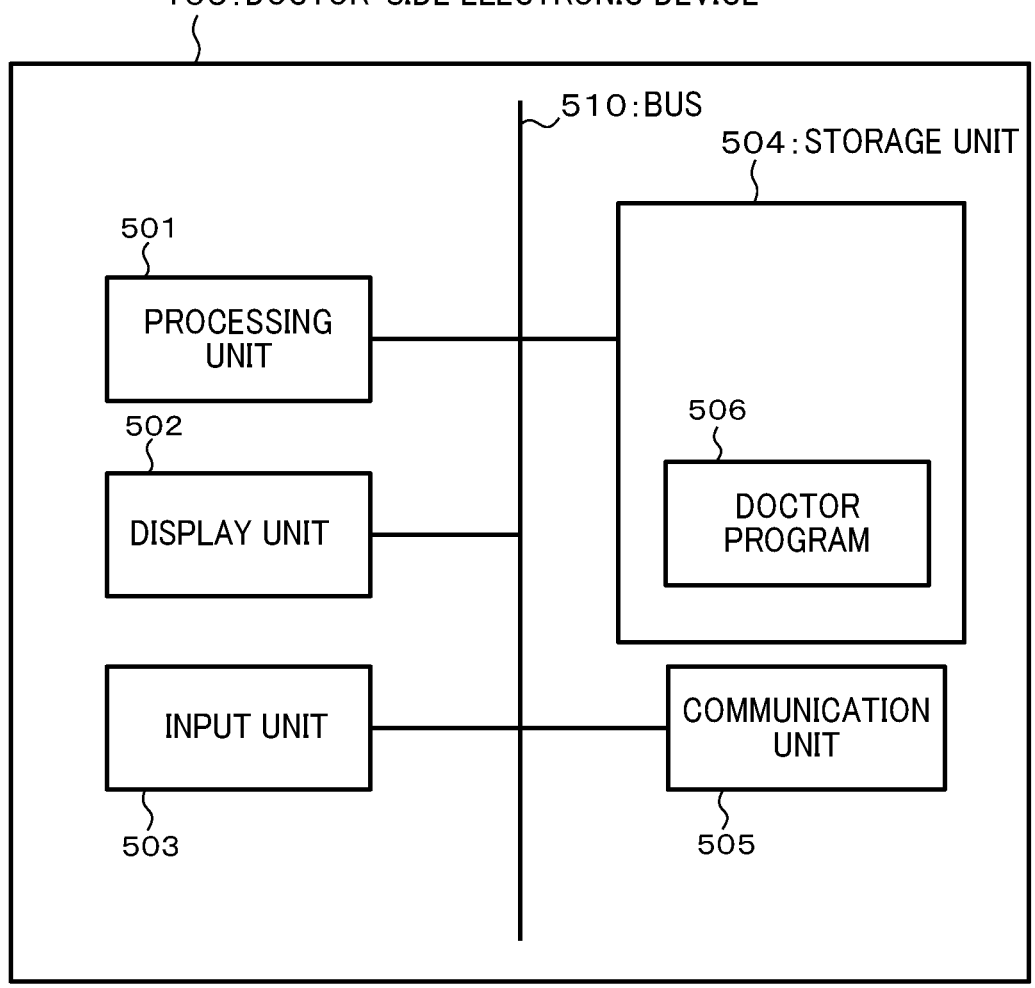
FIG. 5 is a block diagram depicting a hardware configuration of a doctor-side electronic device in the system according to this embodiment.
Figure 6:
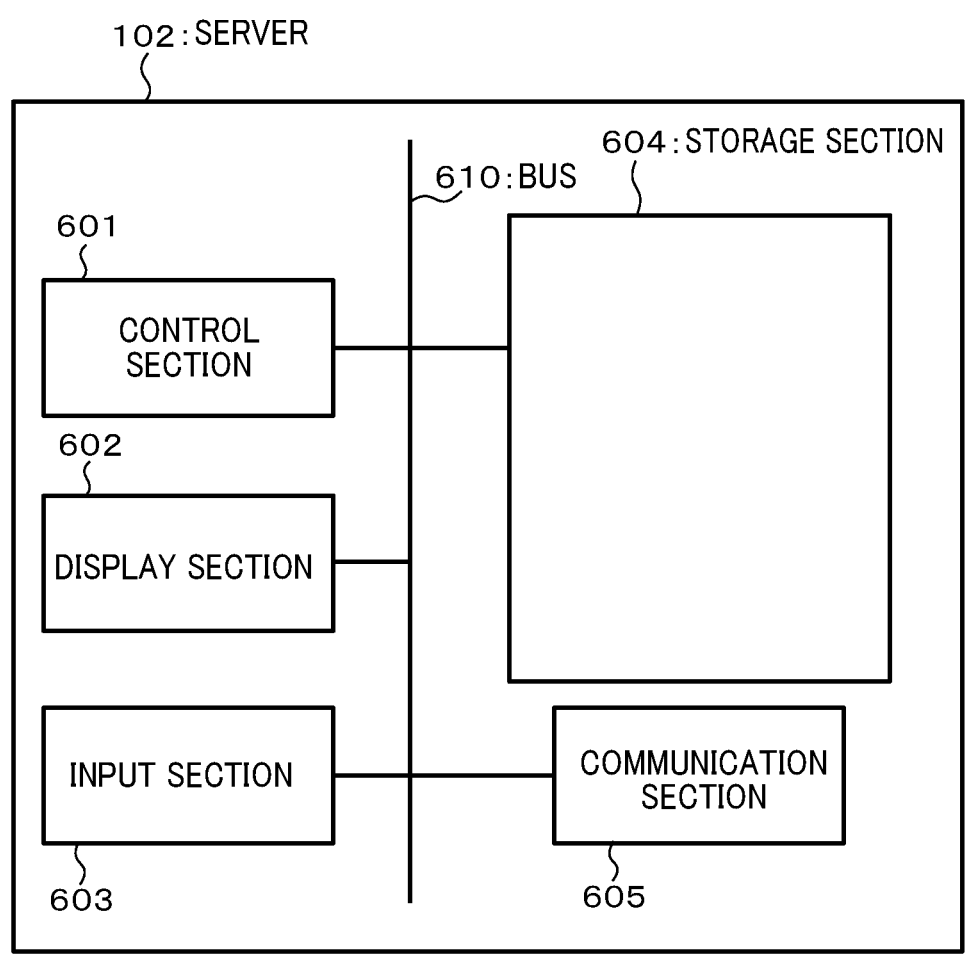
FIG. 6 is a block diagram depicting a functional configuration of the server in the system according to this embodiment.
Figure 7:
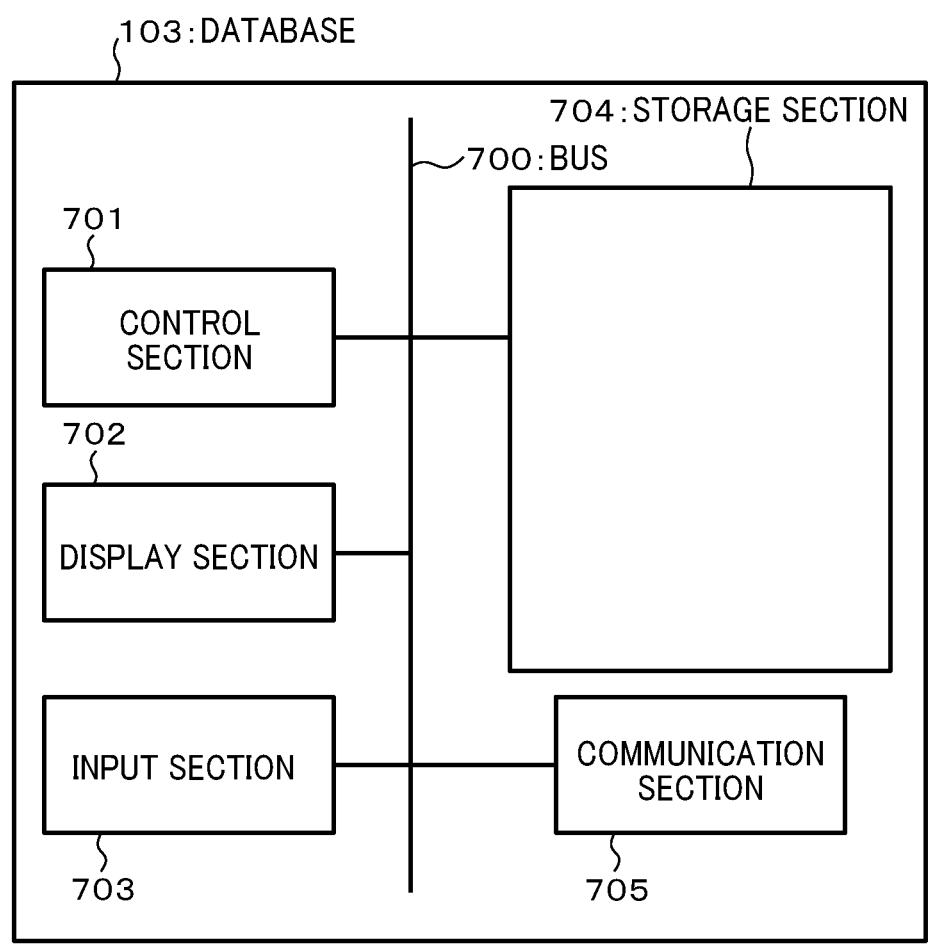
FIG. 7 is a block diagram depicting a functional configuration of the database in the system according to this embodiment.
Figure 8:
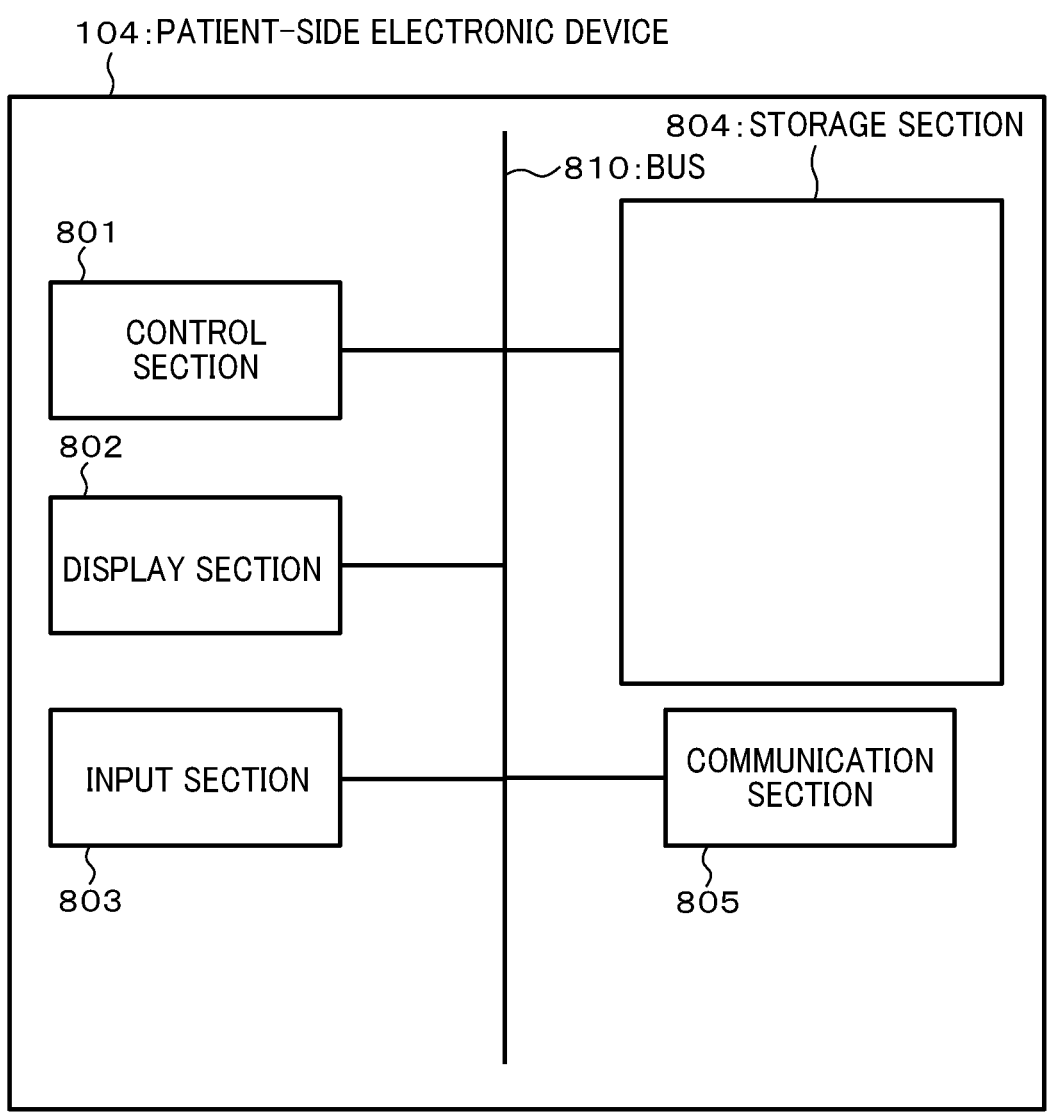
FIG. 8 is a block diagram depicting a functional configuration of the patient-side electronic device in the system according to this embodiment.
Figure 9:
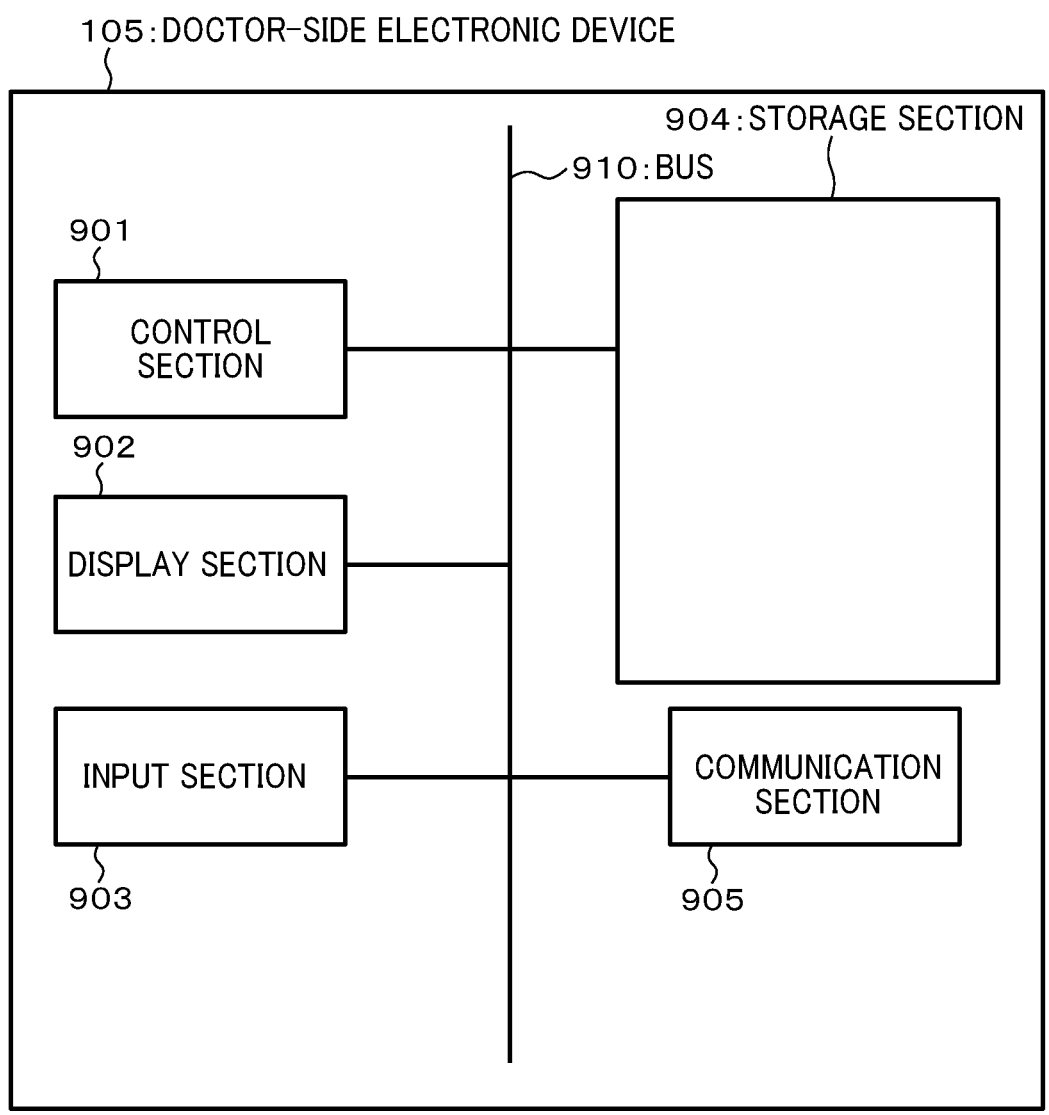
FIG. 9 is a block diagram depicting a functional configuration of the doctor-side electronic device in the system according to this embodiment.

FIG. 5 is a block diagram depicting a hardware configuration of the doctor-side electronic device 105 which is an electronic device used by a doctor, in the system according to this embodiment. The doctor-side electronic device 105 comprises a processing unit 501, a display unit 502, an input unit 503, a storage unit 504, and a communication unit 505. In this embodiment, these units are connected to each other via a bus 510. Alternatively, the doctor-side electronic device may be configured such that they are connected to each other individually as needed basis. The doctor-side electronic device 104 may be composed of a desktop computer or a notebook computer, or may be a personal digital assistance, a mobile phone, a smartphone or a tablet terminal, or may be a dedicated portable electronic device. The display unit 502 has a function of displaying information to a user. The input unit 503 has a function of accepting an input from a user, like a keyboard, a mouse or the like. When the doctor-side electronic device 105 is composed of a smart phone or a tablet terminal, the display unit 502 and the input unit 503 may be integrated together as a touch panel. The storage unit 504 stores therein a doctor program 506 for the doctor-side electronic device. The storage unit 504 may be any type of storage unit, such as a non-volatile memory or a volatile memory, as long as it is capable of storing information therein. The communication unit 505 is operable to perform wire communication using an Ethernet (trademark) cable or the like, or wireless communication using cellular network, wireless LAN or the like, to establish connection to the network 101.

FIGS. 6 to 9 depict respective functional configurations of the server 102, the database 103, the patient-side electronic device 104 and the doctor-side electronic device 105 in the system according to this embodiment. The server 102 comprises a control section 601, a display section 602, an input section 603, a storage section 604 and a communication section 605, and the database 103 comprises a control section 701, a display section 702, an input section 703, a storage section 704 and a communication section 705. The patient-side electronic device 104 comprises a control section 801, a display section 802, an input section 803, a storage section 804 and a communication section 805, and the doctor-side electronic device 105 comprises a control section 901, a display section 902, an input section 903, a storage section 904 and a communication section 905. Each of the control sections operates to execute control such as information processing. Each of the display sections operates to display information in such a manner as to enable a user to visibly recognize the information. Each of the input sections operates to accept an input from a user. Each of the storage sections operates to store therein data or the like. Each of the communication sections operates to transmit and receive information with respect to other devices. In this embodiment, the above functional sections are realized by executing the programs in the hardware described in FIGS. 2 to 5. Alternatively, these functional sections may be realized based on hardware by providing an electronic circuit or the like capable of realizing the functional sections.

In this embodiment, patient information is stored in the storage section 704 of the database 103. The patient information is information related to a patient who is attempting to quit smoking, associated with identification (ID) number of the patient. The patient-related information includes personal information of the patient, smoking cessation-related health-care history information of the patient, etc. As used in this specification, the term "heath care" does not necessarily mean an act performed by a health professional, but may be an act performed based on one or more embodiments of the present invention. In this embodiment, the patient's personal information is basically fixed information, and the smoking cessation-related health-care history information is information which can vary from hour to hour. The patient's personal information includes information such as patient's name, birth date, duration of smoking, starting date of smoking cessation therapy, and trigger for smoking. The smoking cessation-related health-care history information includes information about personal history of smoking cessation-related health-care, such as patient's condition history information, smoking history information, medication history information, and therapy history information. The patient's condition history information is information obtained, for example, by recording patient's conditions on a day-to-day basis, and can be deemed as diary information. The condition history information includes: information about daily conditions, such as having a headache, feeling irritable, feeling good, or feeling nauseous; and a smoking-urge index indicative of a level of urge of smoking. The smoking-urge index can be represented, for example, by the numbers 0 to 5, wherein 0 means a state in which the patient does not have any smoking urge, and 5 means a state in which the patient most strongly has smoking urges. The smoking-urge index is subjectively determined, decided and input by a patient. The smoking history information includes information about whether or not the patient smoked after smoking cessation therapy. For example, in the case where the patient smoked, the smoking history information includes information about the number of smoked cigarettes and date of smoking. The medication history information includes information about an amount of medication taken for smoking cessation therapy and date of the medication. The therapy history information includes history information about a therapy implemented for the patient, such as a cognitive-behavioral therapy implemented by the system, date of the execution, date of recommendation of a behavioral therapy, information indicative of whether or not the patient has actually performed a therapeutic action such as a behavioral therapy, and implemented coaching.

The patient information in this embodiment may be obtained by a medical doctor through patient interview during medical examination, and input and registered in the database 103 via the doctor-side electronic device 105 used by the medical doctor, or may be input and registered in the database 103 via the patient-side electronic device 104 used by the patient. It is to be understood that the two input processes may be combined together. Further, after start of the smoking cessation therapy, the patient information may be updated by any of the above processes.

In aftermentioned embodiments, the patient information is stored in the storage section 704 of the database 103 in association with an identification (ID) number identifying each patient, in the form of a list depicted in FIG. 10. As needed, other necessary information may be appropriately added, and unnecessary information may be not used. In FIG. 10, the personal information includes the following items: name; age; and duration of smoking (year). Further, the smoking cessation-related health-care history information includes the following items: number of days of therapy; smoking-urge index as condition history; smoking history; medication history; and therapy history. The smoking cessation-related health-care history information may be stored together with date. As regards the smoking-urge index, the smoking-urge index 5 means that a patient has a highest level of smoking-urge, and the smoking-urge index 0 means that a patient has a lowest level of smoking-urge. The medication history means a daily situation of medication, wherein 1 means that a patient took medication, and 0 means that a patient did not take any medication. The therapy history presents a history of a therapy implemented for a patient. Each of a plurality of types of therapies is identified by a therapy identification number (ID), and a therapy ID of a therapy implemented is recorded.

In the aftermentioned embodiments, each of the therapies is stored in the storage section 604 of the server 102 in association with the identification number (ID) identifying each therapy, in the form of a therapy list depicted in FIGS. 11A and 11B. Alternatively, the system may be configured such that the therapy list is stored in the storage section 704 of the database 103, and appropriately read by the server 102. The therapy list includes the following items: message; response options; correct response information; therapy type; condition/cause; follow-up; and score. The message is to be displayed in the patient-side electronic device 104, and includes a message for smoking cessation therapy. When the message is an inquiry for a patient (patient inquiry), and a response is requested, the response options are options for response to be displayed in the patient-side electronic device 104. The patient inquiry is intended to inquire about patient's understanding information indicative of understanding of a patient about a smoking-related matter. The correct response information may include the following sub-items: correct option; and guidance information. The correct option means a number of one of the response options which is deemed to be correct. The guidance information is indicative of information which is deemed to be correct with respect to the patient inquiry as a message. Instead of a message based on a simple text, the guidance information may be a moving picture such as an educational video. In this case, the guidance information of the therapy list may include an instruction for reproducing the educational video, and information designating a storage area of the educational video. On the other hand, when the message is not a patient inquiry, the response options and the correct response information are not indispensable. The above information may be presented to a patient, in such a manner that it is output from an audio output section such as a speaker in the form of sound, in addition to being displayed on the display section 802 of the patient-side electronic device 104. The display section may be combined with the audio output section to form an output section.

The therapy type is information indicative of to which of the cognitive-behavioral therapy, the behavioral therapy and the coaching each of the therapy ID corresponds. In FIGS. 11A and 11B, the therapy types "1", "2" and "3" means the cognitive-behavioral therapy, the behavioral therapy and the coaching, respectively. The condition/cause means a condition and its cause triggering implementation of the therapy associated with each therapy ID. In this item, a number on the left (front) side of "/" and a number on the right (rear) side of "I" denote, respectively, to the condition and the cause. In the aftermentioned embodiments, the cause is set in combination with the condition. As regards the condition, "1", "2" and "3" mean a condition in which a patient has smoking urge, a condition in which a patient has a headache, and a condition in which a patient is irritated, respectively. "1" and "2" as the cause of the smoking urge mean stress, and offering of cigarettes by an acquaintance, respectively. That is, "1/1" means that a patient has smoking urge, and its cause is stress. "1" and "2" as the cause of the headache mean a lack of nicotine, and cold, respectively. Further, "0" as the cause means that a patient has not yet been able to specify the cause. In one or more embodiments of the present invention, the cause information is not indispensable. That is, a therapy to be implemented can be specified only by the condition, so that an embodiment devoid of the cause information is also encompassed within the scope of the present invention. A plurality of sets of the condition and the cause can be assigned to one therapy ID. In this case, when a set of a condition and its cause input by a patient corresponds to one of the plurality of sets of the condition and the cause, a therapy associated with the therapy ID will be implemented. The follow-up is information indicative of whether or not it is necessary to execute follow-up processing after a certain therapy is implemented, and, when necessary, a timing at which the follow-up processing is to be executed. For example, the follow-up in each of the therapy IDs 1 to 4 is set to "5". The follow-up "5" means that it is necessary to execute the follow-up processing, wherein the follow-up processing will be executed after 5 minutes since completion of the implementation of the therapy.

The score is information to be used when selecting a therapy to be implemented for a patient, and a reference score is set for each of the condition history (smoking-urge index), the smoking history, the medication history, the therapy history and the number of days of therapy. For example, the smoking history in the therapy ID 1 is set to ">1". This means that a requirement for implementing a therapy associated with the therapy ID 1 comprises a condition in which a patient has smoked one or more cigarettes after start of the therapy. On the other hand, the smoking history "4" means that the therapy associated with the therapy ID 1 is not implemented for a patient for whom this therapy has already been implemented. Each of the condition history (smoking-urge index) and the smoking history in the therapy ID 7 is set to "0*3". This means that a therapy associated with the therapy ID 7 is implemented when a situation where each of the smoking-urge index and the smoking history is 0 is continued for 3 days. The medication history "1*3" means that a requirement for implementing the therapy associated with the therapy ID 7 comprises a condition in which a patient continuously takes a prescribed medicine for 3 days until now. The therapy history "12" means that the requirement for implementing the therapy associated with the therapy ID 7 comprises a condition in which a therapy associated with a therapy ID 12 (not depicted) has been already implemented. The number of days of therapy "28>>21" means that the requirement for implementing the therapy associated with the therapy ID 7 comprises a condition in which the number of days after start of the therapy is greater than 21 and less than 28. In the following embodiments, a therapy satisfying all of the requirements defined by the above scores is selected. Alternatively, the therapy may be implemented when at least one of the requirements is fulfilled, or priorities, weighting factors or the like may be set to respective requirements.

First Embodiment

An operation of a system according to a first embodiment of the present invention will be described. In this embodiment, a smartphone is used as the patient-side electronic device 104, and a notebook-size personal computer is used as the doctor-side electronic device 105. In the following embodiments, only for the sake of explanation, operations between one patient-side electronic device 104 and one doctor-side electronic device 105 will be described. However, it should be understood that this system may comprise two or more patient-side electronic devices 104 and two or more doctor-side electronic devices 105.

As depicted in FIG. 12, in this embodiment, when a patient operates the patient-side electronic device 104 which is his/her own smartphone, to input information indicative of a current condition of the patient, at least one of behavioral therapy, cognitive-behavioral therapy information and coaching is implemented.

Assume that a patient whose patient ID=0 is "AAAA". When the patient thinks that, after start of smoking cessation therapy, a condition problem associated with the smoking cessation therapy, such as smoking urges and withdrawal symptoms, occurs, the patient touches a nurse call button displayed on the display section 802 of the smart phone as the patient-side electronic device 104 (step S1201). Then, in the patient-side electronic device 104, the control section 801 operates to cause the display section 802 to display thereon a condition input screen for inquiring about a specific state of a current condition (step S1202). In this embodiment, the message "What's happening? 1: Urge to smoke, 2: Headache, 3. Irritation" for prompting the patient to select any of three options about condition is displayed. Any other suitable options about condition, such as difficulty in concentrating, and difficulty in sleeping, may be additionally displayed. Among them, the patient selectively inputs one option indicative of a current condition estimated by the patient, via the input section 803 of the patient-side electronic device 104 (step S1204).

When the patient-side electronic device 104 receives, from the patient, the response which is information indicative of the current condition, the control section 801 operates to detect the response, and then decides, based on the response, whether or not it is necessary to prompt the patient to input a cause of the condition. When necessary, the control section 801 operates to cause the display section 802 to display a cause input screen in conformity to the condition (step S1206). In this embodiment, it is preliminarily decided that respective causes of "1. Urge to smoke" and "2: Headache" are inquired, but a cause of "3. Irritation" is not inquired. An inquiry message is also preliminarily prepared with respect to each of "1. Urge to smoke" and "2: Headache". Here, as one example, assume that the current condition of the patient is a state in which the patient has an urge to smoke, i.e., smoking urge, and the option "1. Urge to smoke" is selected in the step S1202. In response to the selection, the control section 801 operates to cause the display section 802 to display thereon the message "What's a cause of smoking urge? 1: Stress, 2: Offering by acquaintance" and prompt the patient to input the cause (step S1206). Assume that the patient thinks the smoking urge is caused by stress. Thus, the patient selects the option "1. Stress", and inputs the response via the input section 803 (step S1208). Information indicative of the current smoking urge as the current condition of the patient, and the input cause is transmitted to the server 102 via the communication section 805, together with a patient ID (0) for identifying this patient (step S1210). The steps S1201 to S1206 may be executed, for example, by an interactive mode configured such that the patient-side electronic device 104 transmits information indicative of a touch to the nurse call button, to the server 102, and responsively the server 102 transmits information for display of a condition input screen, to the patient-side electronic device 104.

In the server 102, when the communication section 605 receives information indicative of the patient ID, the current condition of the patient and the cause (step S1212), the control section 601 operates to transmit a transmission request for patient information about the patient identified based on the received patient ID, to the database 103 via the communication section 605 (step S1214). In the database 103, when the communication section 705 receives the transmission request (step S1216), the control section 701 operates to retrieve patient information about the patient, from the storage section 704, based on the patient ID reconceived together with the patient information transmission request (step S1218), and transmit the patient information to the server 102 (step S1220).

In the server 102, when the communication section 605 receives the patient information from the server 102 (step S1222), the control section 601 operates to select, from the therapy list stored in the storage section 604, a therapy appropriate to the current condition of the patient, based on the received patient information and the cause of the smoking urge. In this embodiment, the patient AAAA currently has smoking urge, and thinks that a cause of the smoking urge is stress. Further, this patient has smoked one or more cigarettes after start of the therapy. Thus, therapies associated with the therapy IDs 1 and 3 to 5 can be selected. Although all of the therapies may be implemented, the number of the therapies may be limited to a given value. In this embodiment, each of a maximum number of cognitive-behavioral therapies, a maximum of behavioral therapies and a maximum of coachings is set to one. In this embodiment, therapies associated with the therapy ID 1, the therapy ID 3 and the therapy ID 5, are selected as cognitive-behavioral therapy, behavioral therapy and coaching, respectively. Although both therapies associated with each the therapy IDs 3 and 4 are behavioral therapy, one of them is randomly selected. Alternatively, the therapy may be selected according to a given rule.

Further, the control section 601 of the server 102 operates to decide an implementation sequence of the selected three therapies, according to a given rule. In this embodiment, according to a rule that behavioral therapy, coaching and cognitive-behavioral therapy are implemented in this order, behavioral therapy in the therapy ID 3, coaching in the therapy ID 5 and cognitive-behavioral therapy in the therapy ID 1 are implemented in this order. By implementing these therapies in this order, it becomes possible to effectively improve the current condition and continue the smoking cessation therapy. For example, substitutive behavioral therapy appropriate to a currently-occurring smoking urge and its cause may be implemented so as to stop or relieve the current smoking urge. Further, coaching can be implemented to encourage the patient to lead the patient to a psychological state free from increasing smoking urges again. Then, after mitigating the smoking urge, cognitive-behavioral therapy is implemented so as to correct understanding of the patient about the previously-occurring smoking urge and its cause, when it is incorrect. This makes it possible to provide better understanding and awareness of the patient, as compared to a situation where cognitive-behavioral therapy is implemented after a relatively long time has elapsed since the occurrence of smoking urge. Thus, it is possible to cut off the incorrectly-understood association between smoking and smoking urge (current condition)/its cause, and thus effectively prevent the patient from reaching the same level of smoking urge again.

The control section 601 of the server 102 operates to reset a counter N to 0 (step S1226), and count up to N (step S1228). Then, the control section 601 operates to implement the therapy (ID "3") as a decided first (N-th) therapy.

An implementation procedure for behavioral therapy and coaching is depicted in FIG. 13. First of all, the control section 601 operates to transmit behavioral therapy information or coaching information indicative of the selected N-th therapy, to the patient-side electronic device 104 via the communication section 605 (step S1301). The behavioral therapy information or coaching information includes a message in the therapy list. At this point, N=1. Thus, an operation of implementing the therapy associated with the therapy ID 3 will be described below. The therapy associated with the therapy ID 3 is behavioral therapy (therapy type 2), and is implemented according to the procedure in FIG. 13. The control section 601 of the server 102 operates to read the therapy list from the storage section 604 and, after adding the message associated with the therapy ID 3 to behavioral therapy information, transmit the resulting behavioral therapy information to the patient-side electronic device 104 (step S1301). Then, in the patient-side electronic device 104, the communication section 805 receives the behavioral therapy information (step S1302), and the control section 801 operates to cause the display section 802 to display thereon the message "Do mild exercise to relieve stress", based on the behavioral therapy information (step S1304). This behavioral therapy is substitutive behavioral therapy intended to instruct a patient to perform a behavior for relieving a currently-occurring smoking urge, other than smoking, to thereby relieve the smoking urge. In this procedure, it is important to, immediately after a patient has smoking urge, specify a cause of the smoking urge, and implement a substitutive behavioral therapy appropriate to the specified cause. This makes it possible to effectively relieve the smoking urge. The patient-side electronic device 104 transmits therapy implementation confirmation information indicative of completion of therapy implementation processing in the patient-side electronic device 104 (step S1306).

In the server 102, upon receiving the therapy implementation confirmation information (step S1308), the control section 601 operates to transmit an update instruction for causing information indicative of implementation of the therapy associated with the therapy ID 3 to be recorded in the therapy history so as to update the therapy history, to the database 103 via the communication section 605 (step S1310). In the database 103, upon receiving the update instruction (step S1312), the control section 701 operates to update the therapy history of the patient AAAA based on the patient ID and the therapy ID (step S1314). Subsequently, in the server 102, follow-up implementation setting processing, i.e., processing of performing setting to implement follow-up, is executed (step S1316). The above update processing may be executed after behavioral therapy information or coaching information is transmitted from the server 102 to the patient-side electronic device 104 and without the transmitting and receiving of the therapy implementation confirmation information. Further, the update processing may be executed after the follow-up implementation setting processing (step S1316).

Figure 14:
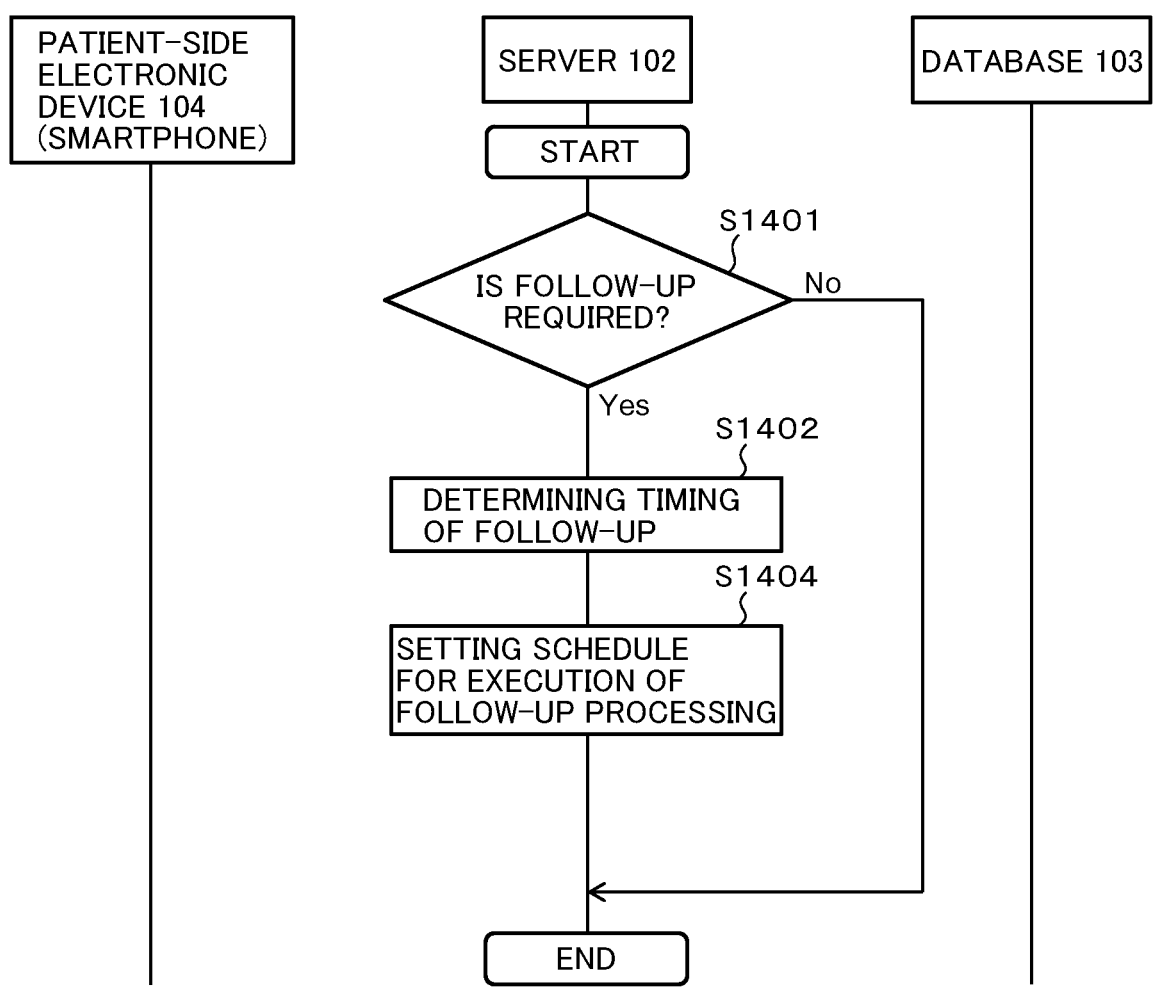
FIG. 14 is a flowchart depicting the process in the system according the first embodiment of the present invention.

Details of the follow-up implementation setting processing (step S1316) will be described based on FIG. 14. First of all, in the server 102, the control section 601 operates to decide, based on the therapy list stored in the storage section 604, whether or not the implemented therapy requires follow-up (step S1401). Referring to the therapy list, the follow-up parameter of the implemented therapy associated with the therapy ID 3 is "5". Thus, the control section 601 of the server 102 operates to decide that the implemented therapy requires follow-up, and a given timing for the follow-up is at 5 minutes after completion of the implementation (steps S1401 and S1402). The control section 601 of the server 102 operates to set a schedule so as to execute the follow-up processing in 5 minutes (step S1404). This processing can be executed as a scheduled execution process such as a cron job.

Figure 15:
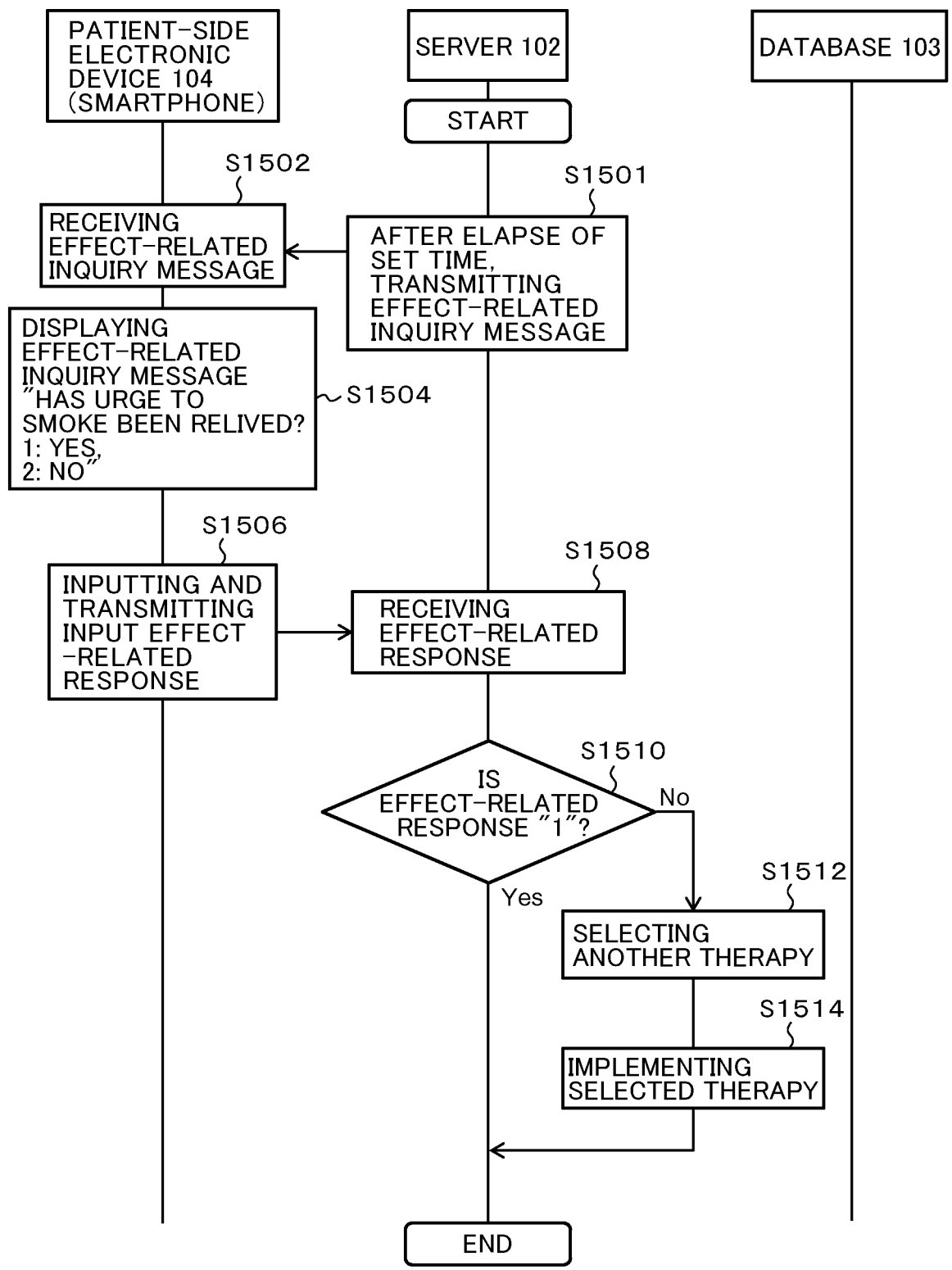
FIG. 15 is a flowchart depicting the process in the system according the first embodiment of the present invention.

Next, the follow-up processing will be described based on FIG. 15. In the server 102, at a scheduled time during the follow-up implementation setting processing, the control section 601 operates to transmit an effect-related inquiry message indicative of a message for inquiring about whether or not a previously-occurring condition is improved (step S1501). In the patient-side electronic device 104, upon receiving the effect-related inquiry message (step S1502), the control section 801 operates to cause the display section 802 to display the effect-related inquiry message thereon. In this embodiment, the message "Has urge to smoke been relived? 1: YES, 2: NO" is displayed. In response to this, the patient touches either one of two buttons "1: YES" and "2: NO" in the input section 603 as a touch panel of the smartphone, to input an effect-related response, and the input effect-related response is transmitted (step S1506). In the server 102, the communication section 605 receives the effect-related response (step S1508), and the control section 601 operates to determine whether or not the effect-related response is "1". When the effect-related response is "1" which means that the previously-occurring smoking urge has been relived, the follow-up processing is terminated. On the other hand, when the effect-related response is "1" which means that the previously-occurring smoking urge has not been yet relived, the control section 601 operates to select an additional therapy for relieving the smoking urge (step S1512), and implement the selected therapy (step S1514). As the additional therapy to be selected, it is possible to select one of the therapies associated with the already implemented therapy, or to implement the same therapy as the already implemented therapy again. Further, one or more therapies may be selected and implemented using the same procedure as the aforementioned steps S1214 to S1232. In this embodiment, the therapy associated with the therapy ID 5 as the additional therapy for relieving stress which is the cause of the currently-occurring smoking charge is selected, and implemented by the steps S1301 to S1316 depicted in FIG. 13. Then, the follow-up processing is terminated. As above, after implementation of the selected therapy, an effect of the therapy can be confirmed at an appropriate timing as needed basis, wherein, when the condition has not been yet improved, an appropriate therapy for improving the condition can be additionally implemented. The follow-up processing may be repeated at given intervals until the condition is improved. Further, the patient-side electronic device 104 may be configured to autonomously display the effect-related message after an elapse of a given time to prompt a patient to input the effect-related response, and then transmit the effect-related response to the server 102.

When the follow-up implementation setting processing (step S1316) is completed, behavioral therapy and coaching implementation processing in FIG. 13 is completed, and the therapy implementation processing in the step S1230 in FIG. 12 is completed. Then, the control section 601 operates to determine whether or not a therapy to be implemented still remains in the selected therapies (step S1232). In the step S1232, K denotes the number of the selected therapies. The setup follow-up processing is processing to be implemented at a given scheduled timing. Thus, a next one of the therapies selected in the step S1224 can be implemented without any need to wait for completion of the follow-up processing.

Further, the server 102 may be configured to, after confirming, in the step S1310, the implementation of behavioral therapy in the patient-side electronic device 104, transmit a message for inquiring about whether or not the patient actually performed the behavioral therapy, and the patient-side electronic device 104 may be configured to present the message to the patient to make an inquiry thereabout. In this case, when the patient selectively input a response to the inquiry about whether or not he/she actually performed, and the response is transmitted from the patient-side electronic device 104 to the server 102. Then, the server 102 transmits the response information to the database 103. For example, in the item "therapy history" of the smoking cessation-related health-care history, in addition to the therapy ID corresponding to the implemented therapy, a sub-item for information about whether or not the patient actually performed the behavioral therapy may be additionally provided, and updated based on information from the server 102. This confirmation processing of confirming whether or not the patient actually performed the behavioral therapy may be composed of a cron job as in the follow-up processing, and may be executed after 5 minutes since completion of the implementation of the therapy. Information about a timing at which the confirmation processing is to be executed may be stored in the therapy list. As regards coaching, the same processing as above may be executed as needed basis.

In the embodiment, three therapies are selected, and therefore K=3. Further, the first processing has been executed up to now, and therefore K=3 and N=1. Thus, K>N is satisfied, so that the routine returns to the step S1228. In the step S1228, N is incremented to 2, and a secondly-selected therapy associated with the therapy ID 5 is implemented (step S1230). As mentioned above, the therapy associated with the therapy ID 5 is coaching. The second therapy is implemented in the steps S1301 to S1316 depicted in FIG. 13, i.e., based on the same procedure as that for behavioral therapy. In the step S1304, instead of the behavioral therapy information, the coaching message "Mr/Miss XX definitely does not buckle under stress!" for encouraging the patient is displayed on the display section 802 of the patient-side electronic device 104. This makes it possible to further encourage the patient whose smoking urge is stopped or relieved by substitutive behavioral therapy, and provide psychological stability. At a time when the coaching implementation processing is completed, K (=3)>N(=2), so that the routine returns to the step S1228. In the step S1228, N is incremented to 3, and cognitive-behavioral therapy which is a thirdly-selected therapy associated with the therapy ID 1 is implemented.

Figure 16:
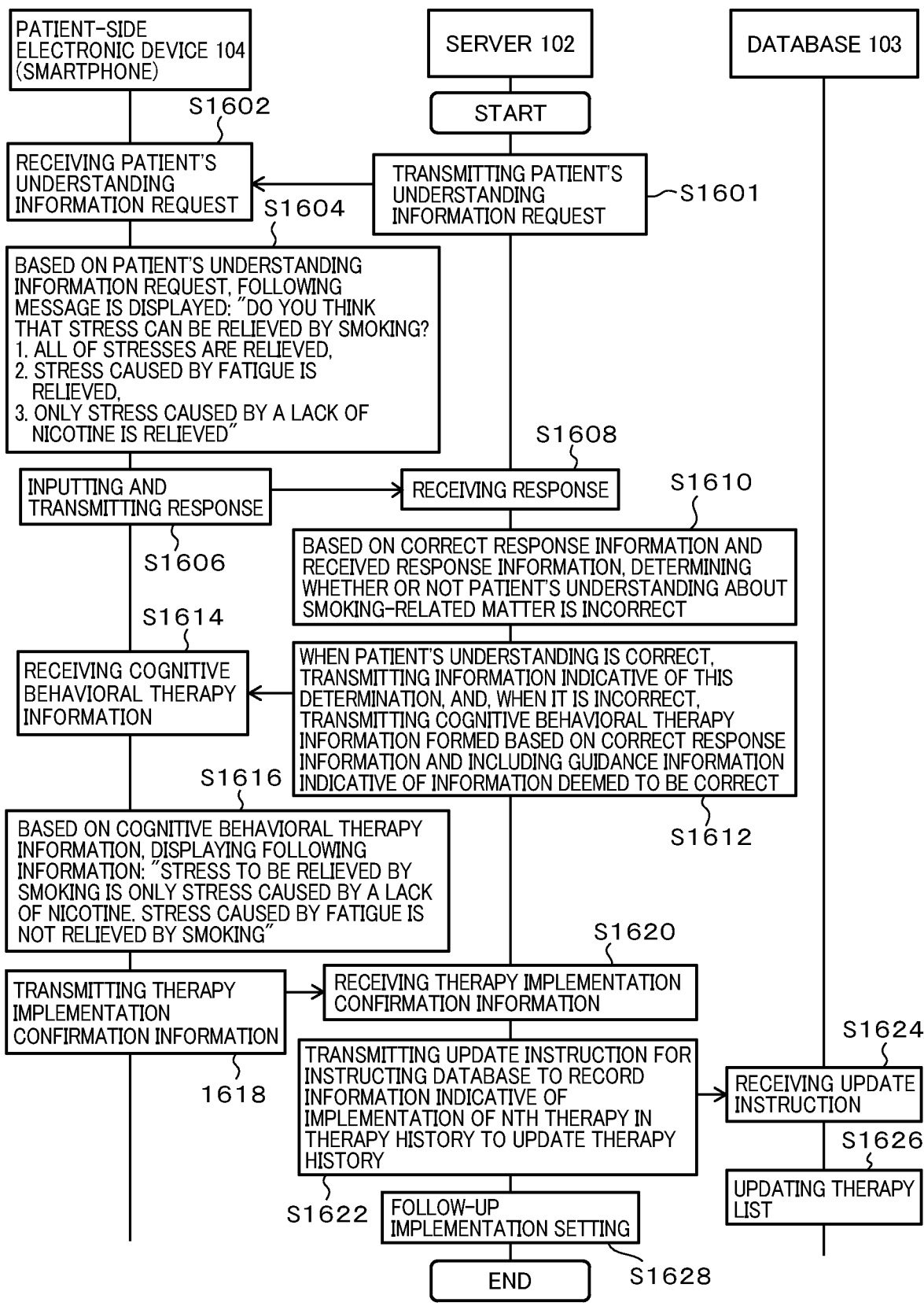
FIG. 16 is a flowchart depicting the process in the system according the first embodiment of the present invention.

A procedure of cognitive-behavioral therapy implementation processing (step S1230) will be described based on FIG. 16. First of all, in step S1601, the control section 601 of the server 102 operates to transmit, to the patient-side electronic device 104, a patient's understanding information request for requesting transmission of patient's understanding information including patient's understanding about a smoking-related matter designated by the selected N-th therapy. The patient's understanding information request includes the message in the therapy list. In the patient-side electronic device 104, upon receiving the patient's understanding information request (step S1602), the control section 801 operates to cause the display section 802 to display thereon a message, based on the received patient's understanding information request (step S1604). In this embodiment, based on message information for the selected cognitive-behavioral therapy associated with the therapy ID 1, the following message for inquiring understanding of the patient about an association between a current condition/its causes and smoking, i.e., a smoking-related matter, is displayed: "Do you think that stress can be relieved by smoking? 1. All of stresses are relieved, 2. Stress caused by fatigue is relieved, 3. Only stress caused by a lack of nicotine is relieved".

In response to this, the patient selectively inputs, as a response, one of the options which is understood as correct by the patient, via the input section 803 of the patient-side electronic device 104, and the input response is transmitted to the server 102 (step S1606). In the server 102, when the communication section 605 receives the response (step S1608), the control section 601 operates to compare the correct response information described in the therapy list with the input response information, so as to decide whether or not the patient's understanding about the smoking-related matter is incorrect (step S1610). Then, the control section 601 operates to, when the patient's understanding is correct, transmit information indicative of this decision, and, when it is incorrect, transmit cognitive behavioral therapy information formed based on the correct response information and including guidance information indicative of information deemed to be correct (step S1612). In the patient-side electronic device 104, upon receiving the cognitive behavioral therapy information (step S1614), the control section 801 operates to cause the display section 802 to display thereon the information deemed to be correct (step S1616).

More specifically, in this embodiment, as the patient's understanding with respect to the following smoking-related matter: "stress can be relieved by smoking?", the patient selectively inputs "1. All of stresses are relieved" as a response, and transmits the response to the server 102, in the step S1606. Then, in the server 102, the control section 601 operates to read the correct response information "3" with reference to the correct response information associated with the therapy ID 1 in the therapy information list. The control section 601 operates to compare the patient's response with the correct response information and determine that they are different, i.e., the patient's understanding is incorrect (step S1610). Then, the control section 601 operates to transmit cognitive behavioral therapy information including guidance information indicative of the guidance information included in the correct response information in the therapy list (step S1612). In the patient-side electronic device 104, upon receiving the cognitive behavioral therapy information, based on the guidance information included therein, the control section 801 operated to cause the display section 802 to display thereon the following message: "Stress to be relieved by smoking is only stress caused by a lack of nicotine. Stress caused by fatigue is not relieved by smoking". In this way, when smoking urge occurs, it is possible to specify its cause and further incorrect understanding of the patient about an association between the smoking urge/the cause and smoking, and correct the patient's incorrect understanding to thereby relieve the smoking urge, and prevent the patient from reaching the same level of smoking urge in the future.

As cognitive-behavioral therapy is implemented at a timing closer to a time when smoking urge occurs, the patient can more easily become aware of his/her incorrect understanding more easily, so that it is possible to increase the effect of the cognitive-behavioral therapy.

When the patient's understanding is correct, for example, the message "That is correct. You understand it very well!" can be displayed. A message for a patient's correct response may be included in the therapy list. Alternatively, a list of messages for a patient's correct response may be separately provided, and one message may be selected therefrom by a given criterion and transmitted to the patient-side electronic device 104 in such a manner that it is included in the cognitive-behavioral therapy information. The message may be any other suitable type of information, as long as it can be presented to the patient in a format capable of informing the patient of a fact that the patient's response is correct.

After implementing the cognitive-behavioral therapy in the step S1616, in the patient-side electronic device 104, the control section 801 operates to transmit therapy implementation confirmation information indicative of completion of the implementation of the therapy (step S1618). In the server 102, upon receiving the therapy implementation confirmation information (step S1620), the control section 601 operates to transmit, to the database 103, an update instruction for instructing the database 103 to record information indicative of implementation of the Nth therapy in the therapy history to update the therapy history (step S1622). In the database 103, upon receiving the update instruction (step S1624), the control section 701 operates to update the therapy history based on the update instruction (step S1626). Subsequently, follow-up implementation setting is executed (step S1628). The update processing may be executed after the cognitive behavioral therapy information is transmitted from the server 102 to the patient-side electronic device 104 and without the transmitting and receiving of the therapy implementation confirmation information, or may be executed after the follow-up implementation setting (step S1628) is executed. The follow-up implementation setting (step S1628) is the same as that described based on FIG. 14.

In the same manner as described in connection with behavioral therapy as the processing of confirming whether or not the patient actually performed the implemented behavioral therapy, the server 102 may be configured to, after confirming, in the step S1622, the implementation of the cognitive-behavioral therapy in the patient-side electronic device 104, transmit an inquiry message for confirming whether or not the incorrect understanding is corrected to the correct understanding by the cognitive-behavioral therapy, and obtain a response from the patient. In this case, the server 102 can transmit the obtained information to the database 103 to update the smoking cessation-related healthcare history.

When the follow-up implementation setting (step S1628) is completed, cognitive-behavioral therapy implementation processing is completed. Thus, at the step S1232, the control section 601 operates to decide whether or not a therapy to be implemented still remains in the pre-selected therapies. At this time, K=3, and N=3, so that K>N is not satisfied. Thus, it is determined that all of the selected therapies have been implemented, and the processing procedure triggered by the patient's touch to the nurse call button is terminated.

The plurality of selected therapies may be configured such that after an elapse of a given time since completion of implementation of one of the therapies, a second one of the therapies is implemented.

The above embodiment has been described based on one example where each of behavioral therapy, coaching and cognitive-behavioral therapy is selected as one of a plurality of therapies, and the resulting total three therapies are implemented. Alternatively, the plurality of therapies may be composed using any one of or any combination of the three types of therapies. Further, two or more therapies, e.g., three therapies, may be selected from each of the three types of therapies. In this case, it is apparent that the system can be operated in the same manner.

In this embodiment, the entire processing can be repeatedly executed. For example, when information indicative of smoking urge is input from a patient at a certain timing, only cognitive-behavioral therapy may be implemented, and then when information indicative of another smoking urge is input from the patient at a different timing, only behavioral therapy may be implemented.

In the first embodiment according the present invention, when a patient reaches a given condition in connection with smoking, it is possible to specify the condition and its cause and timely implement smoking cessation therapy appropriate to the specified condition and cause, to thereby effectively perform smoking cessation therapy. In addition, behavioral therapy, coaching and cognitive-behavioral therapy can be implemented in combination to obtain greater effects. For example, by implementing substitutive behavioral therapy appropriate to currently-occurring smoking urge, it is possible to stop or relieve the smoking urge, and by implementing coaching, it is possible to psychologically support motivation of the patient to quit smoking. As a result, when the patient becomes psychologically stable, cognitive-behavioral therapy can be implemented to correct incorrect understanding of the patient about an association between the previously-occurring smoking urge/its cause and smoking to prevent the patient from reaching the same level of smoking urge again. The same effect can be obtained by a combination of behavioral therapy and cognitive-behavioral therapy or a combination of coaching and cognitive-behavioral therapy.

The notebook-size personal computer as the doctor-side electronic device 105 used by a medical doctor is also connected to the server 102 via the network 101. An information transmission request with identification information of a patient read from the storage section 904 of the doctor-side electronic device 105 is transmitted from the doctor-side electronic device 105. In the server 102, upon receiving the information transmission request, the control section 601 operates to extract patient information stored in the database 103 and associated with the identification information of the patient, and transmit the patient information to the doctor-side electronic device 105. In this way, the medical doctor can check the smoking cessation-related health-care history information which is updated from hour to hour.

Further, the server 102 may be configured such that, when the smoking cessation-related health-care history information is updated after implementation of behavioral therapy, cognitive-behavioral therapy and coaching, or when the smoking cessation-related health-care history information is updated is updated by a patient, the control section 601 operates to detect the update, and execute medication adjustment processing. For example, the control section 601 of the server 102 is operable, when it detects the update of the smoking cessation-related health-care history information, to receive the smoking cessation-related health-care history information from the database 103, based on a patient ID for identifying a patient associated with the updated history information, and decide information about medication adjustment based on the received smoking cessation-related health-care history information, and then to transmit the information about medication adjustment to the doctor-side electronic device 105 used by the medical doctor and/or the patient-side electronic device 104.

In the system according to the first embodiment, an appropriate therapy is implemented depending on a patient condition which varies from hour to hour, so that among patients, a large difference is likely to occur in progress of smoking cessation therapy. A patient who takes an appropriate behavior in conformity to implementation of an appropriate therapy can significantly get an effect of smoking cessation therapy, whereas a patient who smokes a cigarette when smoking urge occurs, without pressing the nurse call button cannot expect to have much effect. Therefore, when the system according to the first embodiment is used, there are greater a difference in effect of smoking cessation therapy among individual persons becomes greater than ever before. Therefore, by implementing medication adjustment based on the smoking cessation-related health-care history information varying from hour to hour, it becomes possible to take a medicine in conformity to progress of smoking cessation therapy in each patient, thereby improving the effect of smoking cessation therapy. Further, medicine side-effect history information may be included in the smoking cessation-related health-care history information. In this case, it becomes possible to perform the medication adjustment based on the medicine side-effect history information so as to minimize a risk of medicine side-effect.

Although this embodiment has been described by taking a situation where smoking urge occurs, as an example of a current condition of a patient, the smoking cessation therapy can also be implemented in the same procedure in a situation where the symptom "2. Headache" occurs as a withdrawal symptom. Specifically, when a patient selects "2. Headache" in the step S1204 among the conditions displayed on the display section 802 in the step S1202, the patient-side electronic device 104 is operable to decide that this option requires an inquiry about its cause, and display a given cause input message on the display section 802 (step S1206). For example, when the message "What's a cause of headache? 1: Lack of nicotine, 2: Cold" is displayed on the display section 802 (step S1206), and the patient selects "1. Lack of nicotine" (step S1208), "2. Headache" and "1. Lack of nicotine" are transmitted to the server 102, as the information indicative of the current condition of the patient and the information indicative of its cause, respectively (step S1210). Based on the received condition and cause information and the patient information acquired in the steps D1212 to S1222, each of the therapies is selected and implemented in the steps S1224 to S1232. In this case, the condition and cause are "2/1" (headache/lack of nicotine). Thus, for example, behavioral therapy associated with the therapy ID 9 corresponding to "2/1" is implemented, and the message "9. Do you think that it is a good way to tentatively relieve headache by smoking a cigarette? 1. YES, 2. NO" is displayed in the patient-side electronic device 104. When a response of the patient to the message is "2" which is incorrect, the message "The occurrence of headache due to a lack of nicotine is a symptom occurring in a course in which your brain changes to a normal state, and is a temporary symptom. If you smoke a cigarette now, your brain will return to a nicotine-dependent state." is presented to the patient as correct information. In this way, the patient's understanding can be corrected.

It should be noted that the cause of the condition is not necessarily specified. For example, when "3. Irritation" as a withdrawal symptom is selected in the step S1204 for inputting a condition, the steps S1206 to S1208 for specifying a cause of the irritation may be omitted. In this case, in the step S1210, only the current condition "Irritation" is transmitted to the server 102. Then, in the step S1224, one of the therapies to be implemented is selected based on the condition "Irritation" and the patient information. For example, in the therapy list, the item "condition/cause" for a therapy which can be implemented under the condition that the condition is "Irritation" and its cause is not specified is described as "3/0". This, behavioral therapy associated with the therapy ID 3 corresponding to "3/0" is implemented, and the message "Do mild exercise to relieve stress" is displayed in the patient-side electronic device 104. In the same manner, cognitive-behavioral therapy or coaching can be implemented without specifying a cause.

Second Embodiment

A second embodiment of the present invention is different from the first embodiment in that a smoking cessation therapy implementation processing is started at a timing decided by the server 102 based on the smoking cessation-related health-care history information of a patient, instead of being started by an input of information indicative of a current condition of the patient. The remaining configuration is the same as that in the first embodiment. The following description will be made about only the difference from the first embodiment.

Figure 17:
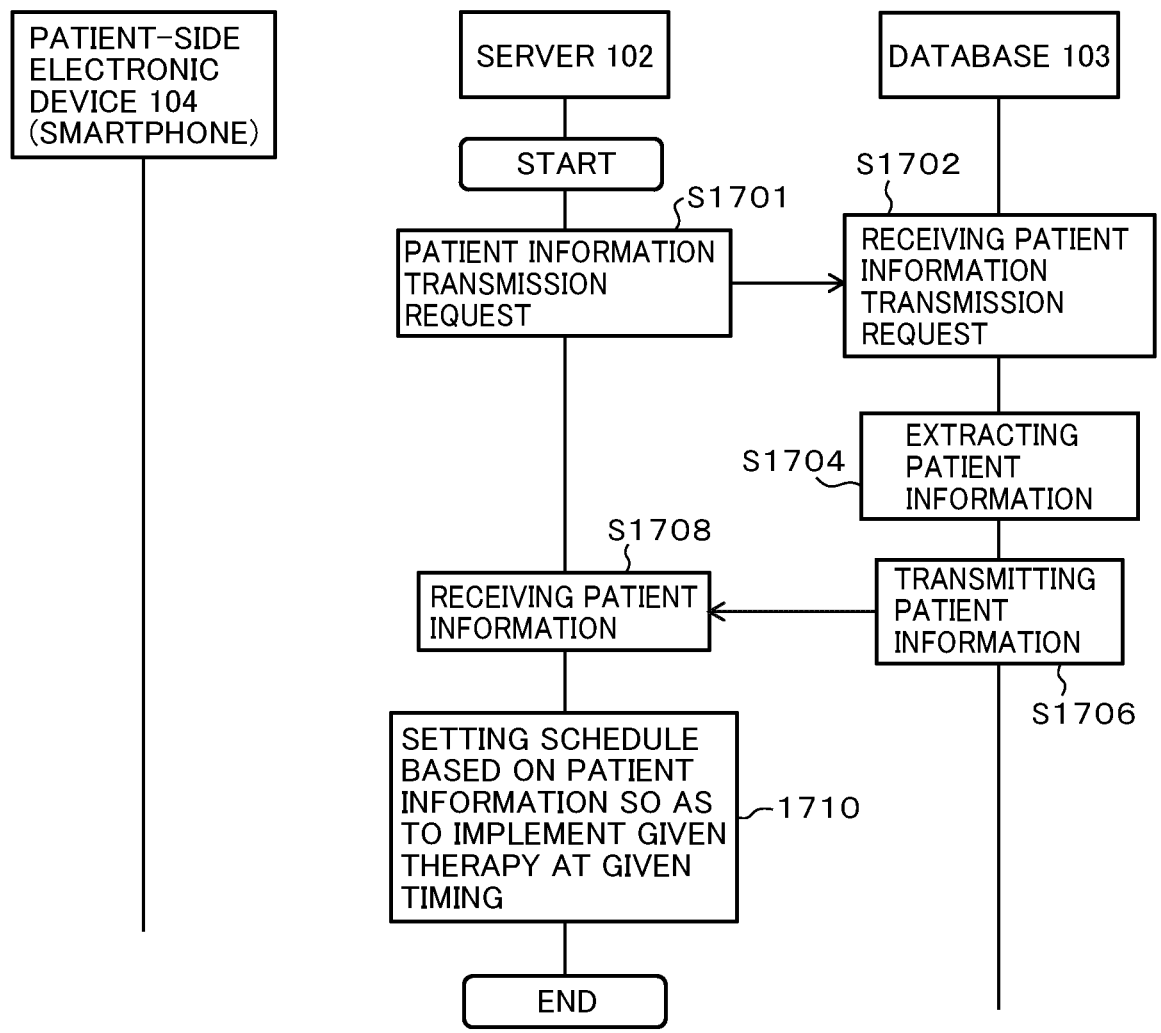
FIG. 17 is a flowchart depicting a process in a system according a second embodiment of the present invention.

With reference to FIG. 17, a processing for setting a schedule so as to implement a given therapy by the server 102 based on patient information at a given timing. First of all, the server 102 transmits a patient information transmission request to the database 103 at a given timing (step S1701). The given timing may be timing set at intervals of a constant period of time, e.g., 24 hours, or may be a given clock time, e.g., 12 a.m. or may be a time when the patient information is updated, or may be a combination of two or more of them. For example, the update of the patient information is executed when a certain therapy is implemented as mentioned above, or is executed by the database 103, based on information about daily condition, status of smoking cessation, status of medication and others, transmitted from the patient to the server 102.

In the database 103, upon receiving the patient information transmission request, the control section 701 operates to extract patient information from the storage section 704 and transmit the patient information to the server 102. The extraction of the patient information may be performed for all patients in a lump, or may be performed one or more patient specified by a patient ID transmitted from the server 102 together with the patient information transmission request. In the server 102, upon receiving the patient information (step S1708), the control section 601 operates to set a schedule so as to implement a given therapy based on the patient information at a given timing (step S1710). As with the scheduling of the follow-up processing (step S1404), this scheduling processing may be set as a scheduled execution processing such as a cron job. Scheduled therapies may be stored in the storage section 604 of the server 102 in the form of a therapy scheduling table. The number of therapies which are scheduled to be implemented at the same timing may be two or more. This scheduling processing is executed based on at least the smoking cessation-related health-care history information in the patient information. Specifically, the scheduling processing is based on the smoking cessation-related health-care history information such as condition history, smoking history, medication history, therapy history, and the number of days of health care, which vary from hour to hour, so that it becomes possible to implement an optimal therapy at an optimal timing for the patient. In addition thereto, fixed personal information may be considered. The scheduled timing may be timing after an elapse of 0 second, i.e., immediate timing, or may be timing after an elapse of 1 hour, or 9 a.m. tomorrow. When the therapy list includes information for deciding an appropriate timing, the scheduled timing may be set based on this information.

For example, when the patient AAAA whose patient ID is 1 has performed update of information indicating that the smoking-urge index on April 3 is 0, via the server 102, as a part of update of a quitting smoking diary, the server 102 is operable to transmit a request for updating the smoking cessation-related health-care history information of the patient AAAA recorded in the database 103. Then, after completion of update in the database 103, the control section 601 of the server 102 operates to transmit, to the database 103 together with the patient ID 1, a request for transmitting the patient information of the patient AAAA (step S1701). In the database 103, upon receiving the request (step S1702), the control section 701 operates to extract the patient information associated with the patient ID 1 (step S1704), and transmit the patient information to the server 102 (step S1706). In the server 102, the control section 601 operates to select a therapy to be implemented, based on the received patient information, and set a schedule so as to implement the select therapy at a given timing. In this embodiment, based on the conditions: condition history (smoking urge index) of the patient AAAA is 0 for the third day from April 1 to April 3; only a therapy associated with the therapy ID 12 has been implemented; and the number of days of therapy is greater than 21 and less than 28, a therapy associated with the therapy ID 7 is selected, and a scheduled time is set to 1 minute so as to quickly implement this therapy. In the second embodiment, there is no input of a current condition and its cause from a patient. Thus, a therapy having no restriction by the item "condition/cause" is selected. It should be understood that a therapy may be selected in disregard of the item "condition/cause".

Figure 18:
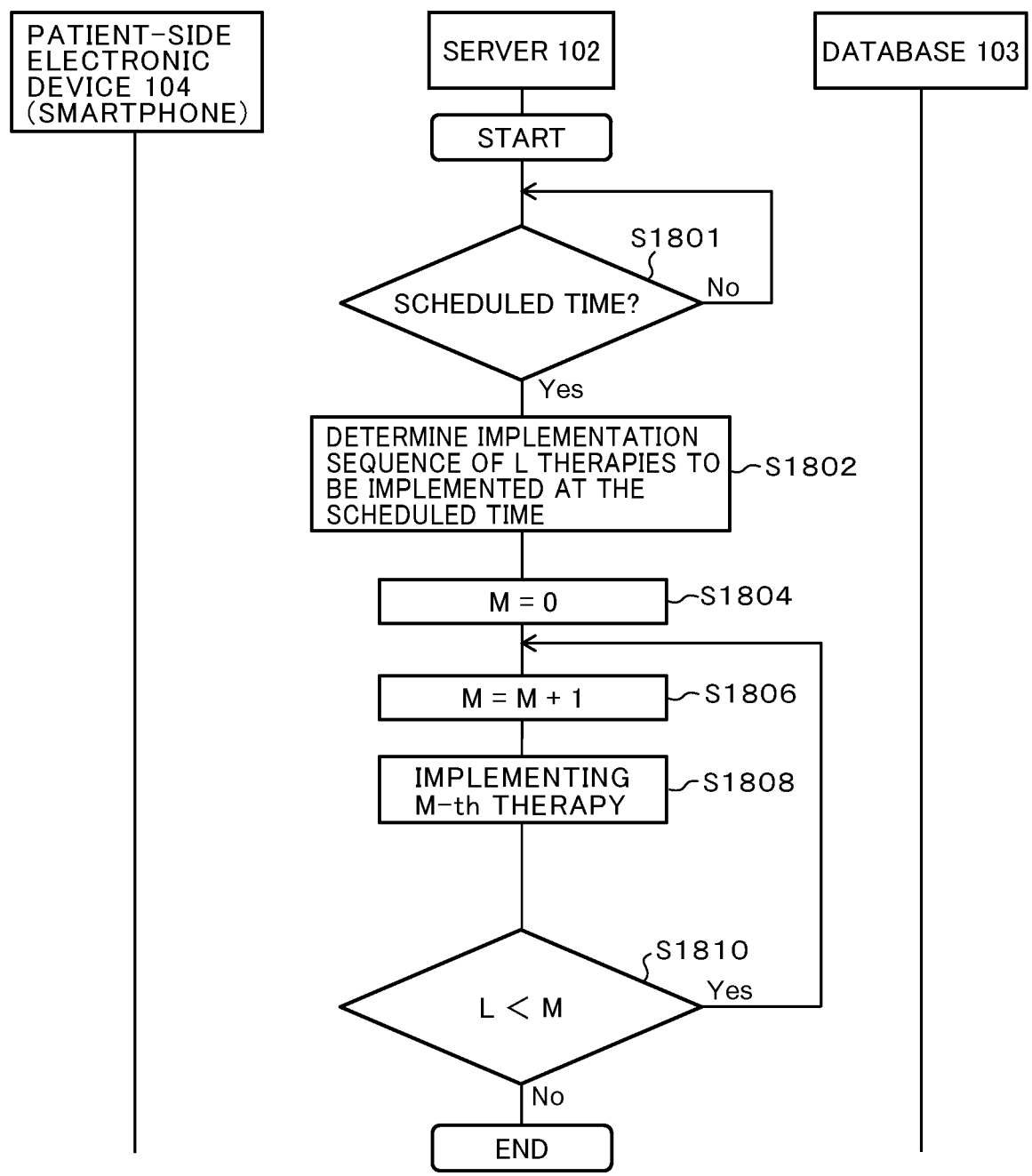
FIG. 18 is a flowchart depicting the process in the system according the second embodiment of the present invention.

As depicted in FIG. 18, in the server 102, the control section 601 operates to keep a standby state until a scheduled time for implementation of a therapy (step S1801), and decide L pieces of therapies each scheduled so as to be implemented at a scheduled time (step S1802). For example, the L therapies can be decided based on a therapy scheduling table stored in the storage section 604 of the server 102. Then, an implementation sequence of the one or more decided therapies is decided according to a given rule. This may be decided in the same manner as that in the first embodiment. Further, this sequence may be decided by the scheduling processing. In this case, in order of timing of the decision, a first therapy is decided. A counter M is set to 0 (step S1804), and then incremented by 1 for a firstly-decided therapy (step S1806). Then, the decided first therapy is implemented (step S1808). This therapy implementation processing is the same as the processing described based on FIG. 13 with regard to behavioral therapy and coaching, and is the same as the processing described based on FIG. 16 with regard to cognitive-behavioral therapy. After implementation of the first therapy, the number L of the decided therapies and the number M of implemented therapies are compared (step S1808). When the number L of the decided therapies is greater than the number M, the routine returns to the step S1806. In the step S1806, one of the remaining therapies is implemented. On the other hand, when the number L is equal to the number M, all of the decided therapies are determined to be implemented, and the processing of implementing the scheduled therapies is terminated.

For example, in the server 102, the control section 601 operates to, at an implementation time for a therapy associated with the therapy ID 7 and scheduled for the patient AAAA, read the therapy associated with the therapy ID 7 and scheduled at the time, from the therapy scheduling table stored in the storage section 604, and decide to implement the therapy associated with the therapy ID 7 (step S1802). The number of therapies to be implemented is one, so that L=1. Then, after resetting the counter M (step S1804), the counter M is incremented for the implementation of the first therapy (step S1806). Then, in the step S1808, the therapy associated with the therapy ID 7 is implemented. The therapy associated with the therapy ID 7 is cognitive-behavioral therapy. Thus, this therapy is implemented by the processing described based on FIG. 16. In the cognitive-behavioral therapy associated with the therapy ID 7, understanding of the patient about the following smoking-related matter: "whether or not there is no harm in smoking one cigarette" is acquired, and, when the patient has the following incorrect understanding: "there is no harm in smoking one cigarette", the coaching message "Please recognize that "smoking just one cigarette" does not simply mean "smoking only once" but results in a situation where your brain returns to a nicotine-dependent state." is presented to the patient.

In the second embodiment, it is possible to, based on a patient's condition which varies from hour to hour, timely select an appropriate therapy and implement the appropriate therapy at an appropriate timing, thereby more effectively performing smoking cessation therapy. For example, there are many cases where, when smoking cessation therapy is started, the smoking urge index is gradually reduced, and becomes 0 after about 21 to 28 days. In this stage, although the patient usually has no smoking urge, smoking urge can suddenly occur for some reason. Further, in this stage, the patient stops smoking for 20 days or more, so that it is often the case that he/she thinks that there is no harm in smoking one cigarette. In a situation where the patient has such an incorrect understanding, he/she is liable to smoke when smoking urge occurs. If the patient actually smokes, patient's brain returns to its previous state before the smoking cessation therapy, resulting in significant setback in smoking cessation therapy. In the worst case, he/she can give up quitting smoking. Thus, the control section 601 operates to timely decide to implement the cognitive-behavioral therapy associated with the therapy ID 7, and implement this therapy. This makes it possible to correct the incorrect understanding of the patient about the smoking-related matter to effectively prevent smoking due to incorrect understanding that patients in this stage tend to have.

As above, in the second embodiment, it becomes possible to monitor a smoking cessation-related health-care history of a patient on a daily basis, and implement an appropriate therapy each time, thereby implementing smoking cessation therapy delicately.

In addition, for example, after confirming that cognition of a patient changes, behavioral therapy can be implemented under the changed cognition, so that it becomes possible to enhance the effect of the behavioral therapy.

As one example, assume that, in the step S1206, a patient selects "2: Offering by acquaintance" as a cause of smoking urge of the patient. A patient who tends to smoke a cigarette offered by an acquaintance has incorrect cognition that if he/she declines a cigarette offered by an acquaintance, the acquaintance feels bad. When such incorrect cognition is confirmed in the steps S1604 to S11610 after implementation of cognitive-behavioral therapy associated with the therapy ID 2, the message "Almost no person feels bad even if you decline his/her offer of cigarettes. Rather, it is often the case that he/she supports quitting smoking." is presented (step S1616) to correct the incorrect understanding of the patient. In the case where information indicative of implementation of this cognitive-behavioral therapy associated with the therapy ID 2 is set in the therapy list, as one requirement of implementation of a therapy associated with the therapy ID 8, the therapy associated with the therapy ID 8 is implemented at a timing when a fact that the therapy associated with the therapy ID 2 has been implemented at a subsequent timing is confirmed from the smoking cessation-related health-care history information. A sub-item "effect of implemented therapy" may be added to "therapy history" in the therapy list. In this case, when the effect of changing cognition according to the aforementioned procedure is confirmed, in addition to the implementation of the cognitive-behavioral therapy, behavioral therapy appropriate to the change in cognition can be implemented. After the cognitive-behavioral therapy associated with the therapy ID 2 is implemented to cause the patient to understand that almost no person feels bad even if you decline his/her offer of cigarettes, the message "You should prepare a specific way to decline offer of cigarettes" for behavioral therapy is presented. This makes it possible to set an environment in which the patient can wisely decline offering of cigarettes and receive support from the acquaintance, based on correct cognition.

When behavioral therapy is implemented by itself, it can provide only a limited effect. In this embodiment, after a change in cognition occurs based on cognitive-behavioral therapy, behavioral therapy appropriate to the change in cognition can be implemented, so that it becomes possible to improve the effect of the behavioral therapy.

Third Embodiment

A system designed to be used for a patient who is attempting to quit smoking, according to a third embodiment of the present invention, has a function of executing both of a procedure for deciding a start timing of implementing smoking cessation therapy, according to the first embodiment, and a procedure for deciding a start timing of implementing smoking cessation therapy, according to the second embodiment. The first embodiment and the second embodiment are different from each other in terms of a technique of deciding the start timing of implementing smoking cessation therapy. However, by combining the first and second embodiments together, it definitely becomes possible to execute both of the two types of therapy start timing deciding processing so as to implement the therapy at a timing decided by either one of the two types of therapy start timing deciding processing. The remaining configuration is the same as those in the first and second embodiments. At each of the timings, an appropriate therapy may be selected and implemented. For example, a therapy to be started at certain timing may be only cognitive-behavioral therapy, and a therapy to be started at another timing may be only behavioral therapy.

Fourth Embodiment

In a fourth embodiment of the present invention, a patient inputs a text in the patient-side electronic device 104 and transmits information indicative of the text to the server 102. Then, the same information processing as those in the first to third embodiments are executed such that the control section 601 of the server 102 operates to subject the received information to syntax analysis processing or the like to analyze and acquire a patient's response, and compare the patient's response with correct response information. The remaining configuration is the same as those in the first to third second embodiments.

As described above, one or more embodiments provide a non-transitory computer-readable computer medium storing instructions for a patient attempting to quit smoking, the instructions causing a computer to: obtain smoking cessation-related health-care history information of the patient updated by the patient attempting to quit smoking; determine, based on the smoking cessation-related health-care history information, a cognitive-behavioral therapy to be performed, to obtain patient's understanding information about smoking related to the cognitive-behavioral therapy; when a request timing comes, transmit, to a patient-side electronic device, a patient's understanding information request to request for transmission of the patient's understanding information about smoking; receive, from the patient-side electronic device, the patient's understanding information about smoking; determine, by comparing the received patient's understanding information with predetermined correct response information about smoking, whether the patient has a correct patient's understanding about smoking; and when the patient's understanding about smoking is incorrect, transmit, to the patient-side electronic device, cognitive-behavioral therapy information based on the predetermined correct response information.

In one or more embodiments, the instructions further cause the computer to: obtain information about the performed cognitive-behavioral therapy and changes of patient's understanding caused by the cognitive-behavioral therapy, determine a behavioral therapy to be performed based on the performed cognitive-behavioral therapy and the changes of patient's understanding caused by the cognitive-behavioral therapy, and transmit, to the patient-side electronic device, behavioral therapy information of the determined behavioral therapy indicative of a behavior to be taken by the patient.

In one or more embodiments, the requesting timing is determined based on the smoking cessation-related health-care history information.

In one or more embodiments, the smoking cessation-related health-care history information includes at least one of smoking urge index and smoking history, and the request timing is a smoking urge occurring timing which is predicted based on the smoking cessation-related health-care history information.

In one or more embodiments, the patient's understanding about smoking is about an effect on a patient's brain in smoking-cession given by smoking.

In one or more embodiments, the instructions further cause the computer to: after transmitting the cognitive-behavioral therapy information, update the smoking cessation-related health-care history information, based on the patient's understanding information and the cognitive-behavioral therapy information; and based on the updated smoking cessation-related health-care history information, transmit information about medication adjustment, to at least one of a doctor-side electronic device used by a medical doctor and the patient-side electronic device.

One or more embodiments provide a method for helping a patient who is attempting to quit smoking including: obtaining, by a processor, smoking cessation-related health-care history information of the patient updated by the patient attempting to quit smoking; determining, by the processor, based on the smoking cessation-related health-care history information, a cognitive-behavioral therapy to be performed, to obtain patient's understanding information about smoking related to the cognitive-behavioral therapy; when a request timing comes, transmitting, by the processor to a patient-side electronic device, a patient's understanding information request to request for transmission of the patient's understanding information about smoking; receiving, by the processor from the patient-side electronic device, the patient's understanding information about smoking; determining, by the processor, by comparing the received patient's understanding information with predetermined correct response information about smoking, whether the patient has a correct patient's understanding about smoking; and when the patient's understanding about smoking is incorrect, transmitting, by the processor to the patient-side electronic device, cognitive-behavioral therapy information based on the predetermined correct response information.

One or more embodiments provide a system for a patient who is attempting to quit smoking configured to: obtain smoking cessation-related health-care history information of the patient updated by the patient attempting to quit smoking; determine, based on the smoking cessation-related health-care history information, a cognitive-behavioral therapy to be performed to obtain patient's understanding information about smoking related to the cognitive-behavioral therapy; when a request timing comes, request an input of the patient's understanding information about smoking; receive the input of the patient's understanding information about smoking; determine, by comparing the received patient's understanding information with predetermined correct response information about smoking, whether the patient has a correct patient's understanding about smoking; and when the patient's understanding about smoking is incorrect, present, at a patient-side electronic device, cognitive-behavioral therapy information based on the predetermined correct response information.

The above embodiments are shown and described simply by way of example for explaining the present invention, and it is to be understood that the present invention is not limited to the embodiments, but various changes and modifications can be made therein without departing from the spirit and scope of the present invention as set forth in appended claims.

LIST OF REFERENCE SIGNS

100: system
101: network
102: server
103: database
104: patient-side electronic device
105: doctor-side electronic device
201: processing unit
202: display unit
203: input unit
204: storage unit
205: communication unit
206: server program
301: processing unit
302: display unit
303: input unit
304: storage unit
305: communication unit
306: DB program
401: processing unit
402: display unit
403: input unit
404: storage unit
405: communication unit
406: patient program
501: processing unit
502: display unit
503: input unit
504: storage unit
505: communication unit
506: doctor program
601: control section
602: display section
603: input section
604: storage section
605: communication section
701: control section
702: display section
703: input section
704: storage section
705: communication section
801: control section
802: display section
803: input section
804: storage section
805: communication section
901: control section
902: display section
903: input section
904: storage section
905: communication section

The invention claimed is:

1. A non-transitory computer-readable computer medium storing instructions for a patient attempting to quit smoking, the instructions causing a computer to:
   obtain smoking cessation-related health-care history information of the patient updated by the patient attempting to quit smoking;
   determine, based on the smoking cessation-related health-care history information, a cognitive-behavioral therapy to be performed, to obtain patient's understanding information about smoking related to the cognitive-behavioral therapy;
   when a request timing comes, transmit, to a patient-side electronic device, a patient's understanding information request to request for transmission of the patient's understanding information about smoking;
   receive, from the patient-side electronic device, the patient's understanding information about smoking;
   determine, by comparing the received patient's understanding information with predetermined correct response information about smoking, whether the patient has a correct patient's understanding about smoking; and
   when the patient's understanding about smoking is incorrect, transmit, to the patient-side electronic device, cognitive-behavioral therapy information based on the predetermined correct response information.

2. The non-transitory computer-readable computer medium of claim 1, wherein
   the instructions further cause the computer to:
      obtain information about the performed cognitive-behavioral therapy and changes of patient's understanding caused by the cognitive-behavioral therapy,
      determine a behavioral therapy to be performed based on the performed cognitive-behavioral therapy and the changes of patient's understanding caused by the cognitive-behavioral therapy, and
      transmit, to the patient-side electronic device, behavioral therapy information of the determined behavioral therapy indicative of a behavior to be taken by the patient.

3. The non-transitory computer-readable computer medium of claim 1, the requesting timing is determined based on the smoking cessation-related health-care history information.

4. The non-transitory computer-readable computer medium of claim 3, wherein
   the smoking cessation-related health-care history information includes at least one of smoking urge index and smoking history, and
   the request timing is a smoking urge occurring timing which is predicted based on the smoking cessation-related health-care history information.

5. The non-transitory computer-readable computer medium of claim 1, wherein the patient's understanding about smoking is about an effect on a patient's brain in smoking-cession given by smoking.

6. The non-transitory computer-readable computer medium of claim 1, wherein the instructions further cause the computer to:
   after transmitting the cognitive-behavioral therapy information, update the smoking cessation-related health-care history information, based on the patient's understanding information and the cognitive-behavioral therapy information; and
   based on the updated smoking cessation-related health-care history information, transmit information about medication adjustment, to at least one of a doctor-side electronic device used by a medical doctor and the patient-side electronic device.

7. A method for helping a patient who is attempting to quit smoking comprising:
   obtaining, by a processor, smoking cessation-related health-care history information of the patient updated by the patient attempting to quit smoking;
   determining, by the processor, based on the smoking cessation-related health-care history information, a cognitive-behavioral therapy to be performed, to obtain patient's understanding information about smoking related to the cognitive-behavioral therapy;
   when a request timing comes, transmitting, by the processor to a patient-side electronic device, a patient's understanding information request to request for transmission of the patient's understanding information about smoking;
   receiving, by the processor from the patient-side electronic device, the patient's understanding information about smoking;
   determining, by the processor, by comparing the received patient's understanding information with predetermined correct response information about smoking, whether the patient has a correct patient's understanding about smoking; and
   when the patient's understanding about smoking is incorrect, transmitting, by the processor to the patient-side electronic device, cognitive-behavioral therapy information based on the predetermined correct response information.

8. A system for a patient who is attempting to quit smoking, the system being configured to:
   obtain smoking cessation-related health-care history information of the patient updated by the patient attempting to quit smoking;
   determine, based on the smoking cessation-related health-care history information, a cognitive-behavioral therapy to be performed to obtain patient's understanding information about smoking related to the cognitive-behavioral therapy;
   when a request timing comes, request an input of the patient's understanding information about smoking;
   receive the input of the patient's understanding information about smoking;
   determine, by comparing the received patient's understanding information with predetermined correct response information about smoking, whether the patient has a correct patient's understanding about smoking; and
   when the patient's understanding about smoking is incorrect, present, at a patient-side electronic device, cognitive-behavioral therapy information based on the predetermined correct response information.

* * * * *